United States Patent
Jennings

(10) Patent No.: US 12,220,423 B2
(45) Date of Patent: Feb. 11, 2025

(54) COMPOUNDS, DERIVATIVES, AND ANALOGS FOR CANCER

(71) Applicant: HYGIA PHARMACEUTICALS, LLC, Jupiter, FL (US)

(72) Inventor: Barbara Brooke Jennings, Juno Beach (FI)

(73) Assignee: HYGIA PHARMACEUTICALS, LLC, Jupiter, FL (US)

(*) Notice: Subject to any disclaimer, the term of this patent is extended or adjusted under 35 U.S.C. 154(b) by 487 days.

(21) Appl. No.: 17/262,682

(22) PCT Filed: Jul. 24, 2019

(86) PCT No.: PCT/US2019/043227
§ 371 (c)(1),
(2) Date: Jan. 22, 2021

(87) PCT Pub. No.: WO2020/023628
PCT Pub. Date: Jan. 30, 2020

(65) Prior Publication Data
US 2021/0353651 A1    Nov. 18, 2021

Related U.S. Application Data

(60) Provisional application No. 62/702,680, filed on Jul. 24, 2018.

(51) Int. Cl.
*A61K 31/683* (2006.01)
*A61K 31/265* (2006.01)
(Continued)

(52) U.S. Cl.
CPC .......... *A61K 31/683* (2013.01); *A61K 31/265* (2013.01); *A61K 45/06* (2013.01);
(Continued)

(58) Field of Classification Search
CPC .... A61K 31/683; A61K 31/265; A61K 45/06; A61P 35/00; C07C 69/96; C07C 2601/14; C07F 9/117
See application file for complete search history.

(56) References Cited

U.S. PATENT DOCUMENTS

2006/0034145 A1    2/2006  Inuzuka et al.
2009/0214474 A1    8/2009  Jennings

FOREIGN PATENT DOCUMENTS

WO          0000206 A1    1/2000
WO       2005053611 A2    6/2005
(Continued)

OTHER PUBLICATIONS

Gregory M, Catimel B, Yin MX, Condron M, Burgess AW, Holmes ABet al., 2016, Synthesis of a Tethered myo-Inositol (1,3,4,5,6) Pentakisphosphate (IP5) Derivative as a Probe for Biological Studies, Synlett, vol. 27, pp. 121-125, ISSN: 0936-5214 (Year: 2015).*

(Continued)

*Primary Examiner* — Clinton A Brooks
*Assistant Examiner* — Josmalen M. Ph. Ramos-Lewis
(74) *Attorney, Agent, or Firm* — ARENTFOX SCHIFF LLP

(57) ABSTRACT

The instant invention provides for inositol derivatives, analogs, methods of preparation and uses that inhibit oncogenic signaling pathways and genes. In particular, the compounds disclosed selectively inhibit one or two classes and or isoforms of PI3K. The invention also provides for compositions comprising such inhibitory compounds and methods of inhibiting KRAS by administering the compound to a patient in need of treatment of cancer.

13 Claims, 7 Drawing Sheets

(51) Int. Cl.
  *A61K 45/06* (2006.01)
  *A61P 35/00* (2006.01)
  *C07C 69/96* (2006.01)
  *C07F 9/117* (2006.01)
(52) U.S. Cl.
  CPC .............. *A61P 35/00* (2018.01); *C07C 69/96* (2013.01); *C07F 9/117* (2013.01); *C07C 2601/14* (2017.05)

(56) References Cited

FOREIGN PATENT DOCUMENTS

| WO | 2005082914 A2 | 9/2005 |
| WO | 2014065229 A1 | 5/2014 |
| WO | 2014143614 A1 | 9/2014 |

OTHER PUBLICATIONS

Supplementary Partial European Search Report dated Jul. 5, 2022 in European Patent Application No. 19 83 9887.
Meuillet E J et al., "Specific inhibition of the Akt1 pleckstrin homology domain by D-3-deoxy-phosphatidyl-myo-Inositol analogues", Molecular Cancer Therapeutics, American Association for Cancer Research, US, vol. 2, No. 4, Apr. 1, 2003, pp. 389-399.
Chen S: "Development for Anticancer Therapy: Small-Molecule Inhibitors Targeting Protein Kinase B", Reviews in Medicinal Chemistry, Jan. 1, 2013, pp. 1272-1294.
Elsevier Life Sciences IP Limited; Jan. 1, 2005, The University of Texas System: "Modulators of Lysophosphatidic Acid (LPA) Signaling and the Use Thereof", XP055932006.
Karol S Bruzik et al., "Are D- and L-chiro-Phosphoinositides Substrates of Phosphatidylinositol-Specific Phospholipase C?+", Biochemistry, Jan. 1, 1994, pp. 8367-8374.
Elliot T S et al., "A synthesis of dioctanoyl phosphatidylinositol", Tetrahedron Asymmetry, Pergamon Press Ltd, Oxford, GB, vol. 20, No. 24, Dec. 22, 2009, pp. 2809-2813.
Wang Q et al., "Understanding the stereospecific interactions of 3-deoxyphosphatidylinositol derivatives with the PTEN phosphatase domain", Journal of Molecular Graphics and Modelling, Elsevier Science, New York, NY, US, vol. 29, No. 1, Aug. 24, 2010, pp. 102-114.
Hansbro P M et al., "The conformational behaviour of phosphatidylinositol in model membranes: 2H-NMR studies", Biochimica Et Biophysica Acta, Elsevier, Amsterdam, NL, vol. 1112, No. 2, Dec. 9, 1992, pp. 187-196.
Bradshaw J P et al., "Orientation of the headgroup of the phosphatylinositol in a model biomembrane as determined by neutron diffraction", Biochemistry, vol. 38, Jan. 1, 1999, pp. 8393-8401.
Curstedt T et al., "Individual Molecular Species of Phosphatidyl Cholines and Phosphatidyl Inositols in Liver of Rats Fed BIS-2 Ethylhexyl Phthalate", Medical Biology, Duodecim, FI, vol. 61, No. 4, Jan. 1, 1983, pp. 219-222.
Gadola S D et al., "Structure of human CD1b with bound ligands at 2.3 A, a maze for alkyl chains", Nature Immulogy, Nature Publishing Group US, New York, vol. 3, No. 8, Aug. 1, 2002, pp. 721-726.
Colin H MacPhee et al., "The Stereoselective Recognition of Substrates by Phosphoinositide Kinases Studies Using Synthetic Stereoisomers of Dipalmitoyl Phosphatidylinositol*", the Journal of Biological Chemistry, Jun. 5, 1992, pp. 11137-11143.
Database Pubchem Compound [Online], Jul. 19, 2014, "[3-[Hydroxy-(2,3,4,5,6-pentahydroxycyclohexyl) oxyphosphoryl] oxy-2-nonadecanoyloxypropyl] nonadecanoate", XP055682329, 7 pages.
Extended European Search Report dated Feb. 22, 2023 in European Patent Application No. 19839887.7.
Kume Takashi et al., "The study on phosphatidylinositol-Specific Phospholipase C from Bacillus thuringiensis: Synthesis of Homogeneous Substrates, Substrate Specificity and Other Properties", Chem. Pharm. Bull, 1992, 40(8), pp. 2133-2137.
Rebecchi Mario J. et al., Hydrolysis of Short Acyl Chain Inositol Lipids by Phospholipase C-delta 1, The Journal of Biological Chemistry, 1993, vol. 268, No. 3, pp. 1735-1741.
Kubiak Robert et al., "Comprehensive and Uniform Synthesis of all Naturally Occurring Phosphorylated Phosphatidylinositols", Journal of Organic Chemistry, 2003, 68, pp. 960-968.
Ainge Gary D et al., "Chemical Synthesis and Immunosuppressive Activity of Dipalmitoyl Phosphatidylinositol Hexamannoside", Journal of Organic Chemistry, 2011, 76, pp. 4941-4951.
Communication pursuant to Article 94(3) EPC issued in European Application No. 19839887.7, mailed Oct. 18, 2023, 4 pages.
International Search Report and Written Opinion issued in International Application No. PCT/US2019/043227, mailed Nov. 7, 2019.

* cited by examiner

COMPOUNDS, DERIVATIVES, AND ANALOGS FOR CANCER

CROSS-REFERENCE TO RELATED APPLICATIONS

This application is a 35 U.S.C. § 371 U.S. National Stage Entry of International Application No. PCT/US2019/043227, filed on Jul. 24, 2019, which claims the benefit of U.S. Provisional Application No. 62/702,680, filed on Jul. 24, 2018, all of which are incorporated by reference herein in their entireties.

FIELD OF THE INVENTION

The present invention relates to compounds having a core structure selected from myo-inositol, D-chiro-inositol, isomers thereof, deoxy variants of the foregoing, and phosphorylated versions thereof. The present invention relates to monofatty acyl-monoalkoxyglycerophosphatidyl substituted and di-fatty acyl-glycerophosphatidyl substituted versions of the core structure components mentioned above. The invention additionally relates to compounds having an acylated PEG-linking bridge between (1) an unphosphorylated inositol (or unphosphorylated inositol isomer) and (2) a phosphorylated inositol (or inositol isomer). The invention further relates to methods of manufacture of the foregoing. The invention also relates to novel compositions of matter and methods of use of the compounds as for example, upregulators of p53 tumor suppressor and wild-type P53 tumor suppressor and down regulators and/or inhibitors of mutant P53 and KRAS oncogenes. The invention also relates to novel inhibitors of PI3K/AKT/PDK1/mTOR.

BACKGROUND OF THE INVENTION

A growing number of studies have demonstrated that aberrant activation of the PI3K signaling pathway is a common occurrence in many types of cancer. PI3K-signaling is mediated by protein kinase b (Akt). These dually activated pathways have also been implicated in many other disease states including metabolic diseases (diabetes and insulin resistance), inflammation, and cardiovascular diseases, making this an attractive target for drug development. Current PI3K inhibitors in development by others have shown to be quite toxic and non-selective in both pre-clinical and clinical trials due to off target toxicities like hyperglycemia and liver toxicity, (Ihle, T, 2009), ASCO meeting, 2010. However, the use of inositol-based compounds like D-chiro-inositol and/or myo inositol and/or their isomers will likely not have any significant adverse effects on normal cellular pathways because inositols, especially D-chiro-inositol, have been shown in studies to actually have positive effects on insulin signaling, storage, secretion, and glucose disposal, thereby making clinical trial outcomes much more predictable and positive (Larner, J, 2002).

A growing number of studies have demonstrated that sustained activation of the PI3K/AKT pathway is a common occurrence in many types of cancer including lung and pancreatic, for which no effective treatment regimens currently exists. Moreover, several naturally occurring inositols, such as myoinositol and its phosphorylated derivatives, exhibit anti-proliferative and anti-cancer activity in animal models of cancer and in early phase clinical studies, Lam S, et al, 2006. These compounds also exhibit little to no toxicity, which makes them an attractive alternative to other small molecule PI3K inhibitors with unfavorable toxicity profiles Gustafson A M, et al, 2010. As such, several novel inositol derivatives are provided with the expectation of having low toxicity, good selectivity against PI3K activity, and potent anti-proliferative and tumor killing properties.

Mutations in the p53 tumor suppressor gene occur in around 50% of all human cancerous tumors, making it the most frequent target for genetic alterations in cancer. Such mutations facilitate carcinogenesis primarily through blocking the tumor suppressor activities of the wild type p53 protein. Furthermore, there are some forms of tumor-associated mutant p53 proteins that do contribute to overt oncogenic activities. Excessive wild type p53 activity gives rise to a variety of cellular outcomes particularly cell cycle arrest and apoptosis. These cellular effects of wild type p53 can reduce cancer incidence through elimination of cancer-prone cells from the replicative pool. However, such effects might become very undesirable if occurring in a normal, unperturbed cell. Therefore, P53 activity must be kept under tight control, being unleashed only when a cell accumulates lesions that may otherwise drive it into a cancerous state. Reactivation of wild type p53 by novel inositol derivatives small molecules is a very promising potential cancer therapy. These compounds will actively induce tumor suppressor function by fitting into a transient opening of a binding pocket of the p53 core domain, inducing reactivation of tumor suppressor (Wasmann, C D et al, 2013). For more than 30 years, scientists have been studying a gene called KRAS, the genetic driver of pancreatic cancer initiation and propagation. However, at this time, no therapeutic solutions to KRAS mutations have been developed. Boszik et. al (2007), shows myo inositol hexaphosphate down regulates KRAS and other relevant genes significantly with ($p<0.05$) in K-562 cells that were treated with 750 micromolars of IP6 for 60 min (Bozsik et al, 2007).

SUMMARY OF THE INVENTION

Embodiments and principles of the present invention relate to compounds that are inhibitors of PI3K, Akt/mTOR and PDK1 and inhibitors of overactive signaling pathways.

Embodiments and principles of the present invention relate to pharmaceutical formulations comprising the compounds of the present invention.

Embodiments and principles of the present invention relate to a method for treating cancer comprising administering a pharmaceutical formulation of the present invention to a patient in need of treatment for cancer.

Embodiments and principles of the present invention relate to compounds that are up regulators of P53 tumor suppressor and wild type P53 tumor suppressor and down regulators of mutant P53 tumor suppressor.

Embodiments and principles of the present invention relate to pharmaceutical formulations comprising the compounds of the present invention.

Embodiments and principles of the present invention relate to a method for treating cancer comprising administering a pharmaceutical formulation of the present invention to a patient in need of treatment for cancer.

Embodiments and principles of the present invention relate to compounds that are inhibitors or down regulators of the KRAS oncogene.

Embodiments and principles of the present invention relate to pharmaceutical formulations comprising the compounds of the present invention.

Embodiments and principles of the present invention relate to a method for treating cancer comprising administering a pharmaceutical formulation of the present invention to a patient in need of treatment for cancer.

Embodiments and principles of the present invention relate to compounds that are capable of binding to pleckstrin homology (PH) domains.

Embodiments and principles of the present invention relate to pharmaceutical formulations that comprising compounds of the present invention.

Embodiments and principles of the present invention relate to a method for treating cancer comprising administering a pharmaceutical formulation of the present compounds to a patient in need of treatment for cancer.

Embodiments and principles of the present invention relate to synthetic approaches to producing monofatty acyl-monoalkoxyglycerophosphatidyl substituted and di-fatty acyl-glycerophosphatidyl substituted versions of myo-inositol, D-chiro-inositol, isomers thereof, deoxy variants of the foregoing, and phosphorylated versions thereof.

Embodiments of the present invention provide low-toxicity inositol compounds that can inhibit oncogene KRAS, up regulators of P53 tumor suppressor, wild-type P53 tumor suppressor, and down regulators and/or inhibitors of mutant P53 tumor suppressor, PI3KT/AKT/PD1/mTOR, and bind to undruggable pleckstrin homology (PH) domains. In particular, the compounds can selectively inhibit several classes of PI3Kinases and their isoforms, for example (delta, gamma) and one or more of the Akt isoforms.

Embodiments of the present invention can also provide methods of inhibiting oncogenic signaling pathways up regulated in solid and wet tumors by administering a compound described herein to a patient in need of treatment for cancer.

In various embodiments, the compounds can be those of formula I:

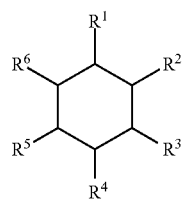

wherein:
one of $R^1$-$R^6$ is —O—Y and five of $R^1$-$R^6$ are OH, or one of $R^1$-$R^6$ is —O—Y, four of $R^1$-$R^6$ are OH and one of $R^1$-$R^6$ is H;
each of $R^1$-$R^6$ may be independently in an axial or an equatorial orientation;
Y is selected from —P(=O)(—OH)—$OR^7$, —C(=O)—$OR^7$, and —C(=O)—$R^8$;
$R^7$ is —$CH_2$—CH($OR^9$)$CH_2OR^{10}$;
$R^8$ is —($CH_2CH_2O$—)$_x$—$CH_2CH_2$—Z;
$R^9$ and $R^{10}$ are independently selected from a $C_1$-$C_6$ alkyl group and a $C_6$-$C_{26}$ acyl group optionally possessing 0-4 double bonds, triple bonds or a combination thereof;
each double bond of $R^9$ and $R^{10}$ may be independently in a cis or a trans orientation; and
x is an integer from 1-6;

Z is a structure of formula II:

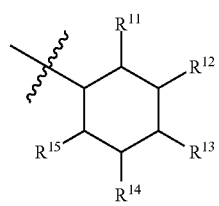

wherein:
each of four of $R^{11}$ through $R^{15}$ is —O—P(=O)(OH)$_2$;
one of $R^{11}$ through $R^{15}$ is selected from benzyloxy and —O—P(=O)(OH)$_2$; and
each of substituent on the ring of formula II may be independently in either an axial or an equatorial orientation.

In various embodiments, a method for producing compounds that include those of formula I is provided:

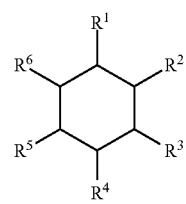

comprising the steps of:
(a) reacting a compound of formula III with a compound of formula IV producing a compound of formula V;

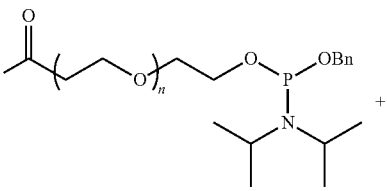

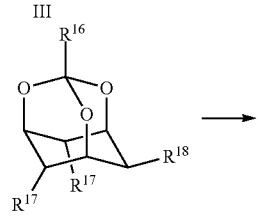

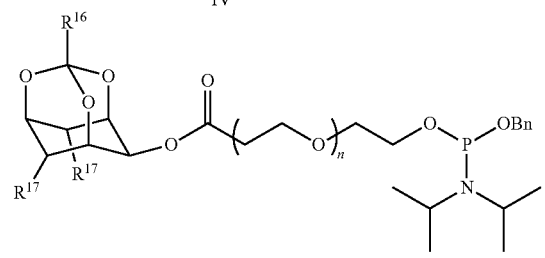

(b) reacting a compound of formula V with a compound of formula VI producing a compound of formula VII;

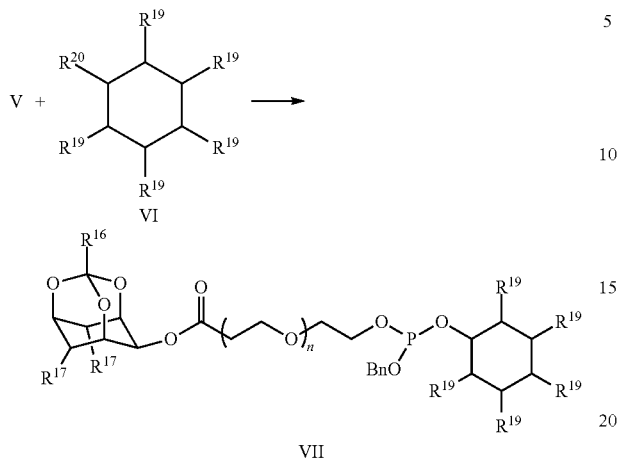

(c) oxidizing a phosphite to a phosphate; and
(d) cleaving all protecting groups,
wherein:
one of $R^1$-$R^6$ is —O—Y and five of $R^1$-$R^6$ are OH;
each of $R^1$-$R^6$ may be independently in an axial or an equatorial orientation;
Y is —C(=O)—$R^8$;
$R^8$ is —(CH$_2$CH$_2$O—)$_x$—CH$_2$CH$_2$—Z;
x is an integer from 1-6;
Z is a structure of formula II:

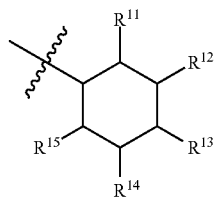

wherein:
each of four of $R^{11}$ through $R^{15}$ is —O—P(=O)(OH)$_2$;
one of $R^{11}$ through $R^{15}$ is selected from benzyloxy and —O—P(=O)(OH)$_2$;
each of substituent on the ring of formula II may be independently in either an axial or an equatorial orientation.
W is a leaving group selected from N-hydroxysuccinimide (NHS), 4-nitrophenol, imidazole, 1-hydroxybenzotriazole (HOBt) and a halide (e.g., chlorine (Cl), bromine (Br), iodine (I));
$R^{16}$ is H, a $C_1$-$C_6$ alkyl, or a phenyl;
each $R^{17}$ is —O-benzyl, —O-TMS (trimethylsilyl), —O-TBDMS (tert-butyldimethylsilyl), —O-TBDPS (tert-butyldiphenylsilyl), —O-(4-methoxybenzyl), acetoxy, or —O-MOM (methoxymethyl);
$R^{18}$ is OH;
each $R^{19}$ is —OP(O)(OBn)$_2$ (Bn=Benzyl);
$R^{20}$ is OH;
each of $R^{17}$, $R^{18}$, $R^{19}$ and $R^{20}$ may be independently in an axial or an equatorial orientation;

protecting groups are independently selected from benzyl ester, benzyl phosphate, orthobenzoate, orthoformate, TBDMS, and MOM; and
n is an integer from 1-6.
In one or more embodiments, a method for producing compounds that include those of formula I is provided:

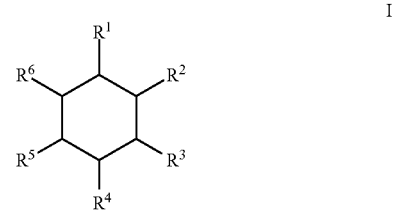

comprising the steps of:
(a) reacting a compound of formula VIII with a compound of formula IX producing a compound of formula X;

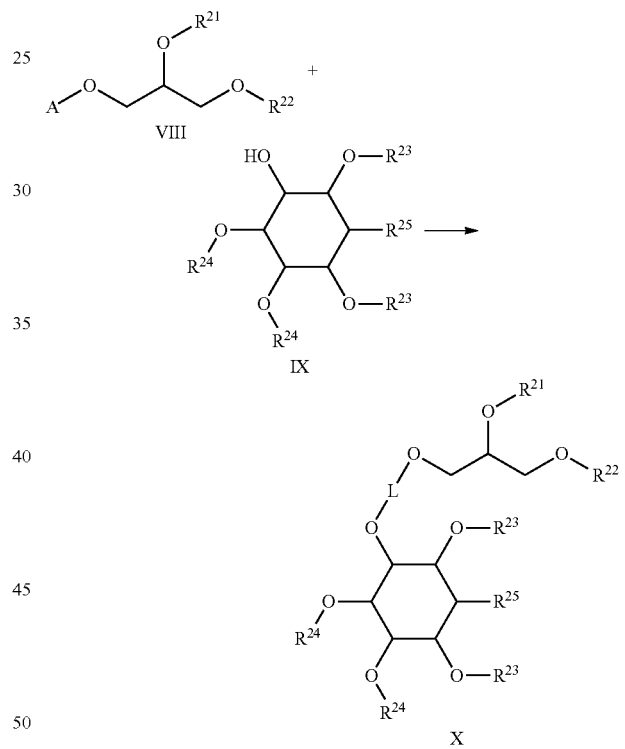

(b) optionally oxidizing a phosphite to a phosphate; and
(c) cleaving all protecting groups,
wherein:
one of $R^1$-$R^6$ is —O—Y and five of $R^1$-$R^6$ are OH, or one of $R^1$-$R^6$ is —O—Y, four of $R^1$-$R^6$ are OH and one of $R^1$-$R^6$ is H;
each of $R^1$-$R^6$ may be independently in an axial or an equatorial orientation;
Y is selected from —P(=O)(—OH)—$OR^7$ and —C(=O)—$OR^7$;
$R^7$ is —CH$_2$—CH($OR^9$)CH$_2OR^{10}$;
$R^9$ and $R^{10}$ are independently selected from a $C_1$-$C_6$ alkyl group and a $C_6$-$C_{26}$ acyl group optionally possessing 0-4 double bonds, triple bonds or a combination thereof;

each double bond of $R^9$ and $R^{10}$ may be independently in a cis or a trans orientation;

$R^{21}$ and $R^{22}$ are independently selected from a $C_1$-$C_6$ alkyl group and a $C_6$-$C_{26}$ acyl group optionally possessing 0-4 double bonds, triple bonds or a combination thereof;

each $R^{23}$ is independently selected from benzyl, TBDMS, 4-methoxybenzyl, and MOM;

each $R^{24}$ is MOM or each $R^{24}$ is covalently linked to one another forming a di-acetal protecting group;

$R^{25}$ is H, —O-MOM, —O-benzyl, —O-TBDMS, or —O-(4-methoxybenzyl);

A is

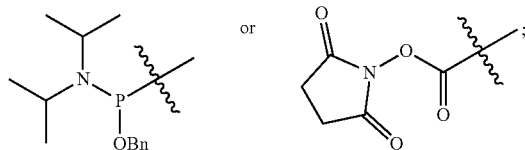 [SMILES: *P(OCc1ccccc1)N(C(C)C)C(C)C ; *C(=O)ON1C(=O)CCC1=O]

L is C=O or P—OBn; and all ring substituents may be independently in an axial or an equatorial orientation.

Embodiments of the present invention further provide methods of treating cancer in a subject in need of treatment, comprising administering to the subject a therapeutically effective amount of a compound described herein, such as a compound of formula I, more particularly without limitation the compounds of Formulae XI, XII, XIII, XIV, XV or XVI and compounds of Formulas A-F, 12, 35, 37, 40, and 56 of the synthesis schemes shown in the drawings attached hereto. In one embodiment, the subject is a mammal. In more preferred embodiments, the subject is a human.

The disclosure further provides a method of reducing the proliferation of cancer cells, comprising contacting the cancer cell, an oncogene, or a signaling pathway with an therapeutically effective amount of a compound described herein, such as a compound of formula XI, XII, XIII, XIV, XV or XVI and compounds of Formulas A-F, 12, 35, 37, 40, and 56 of the synthesis schemes shown in the drawings attached hereto.

DETAILED DESCRIPTION OF THE INVENTION

Figure 1:
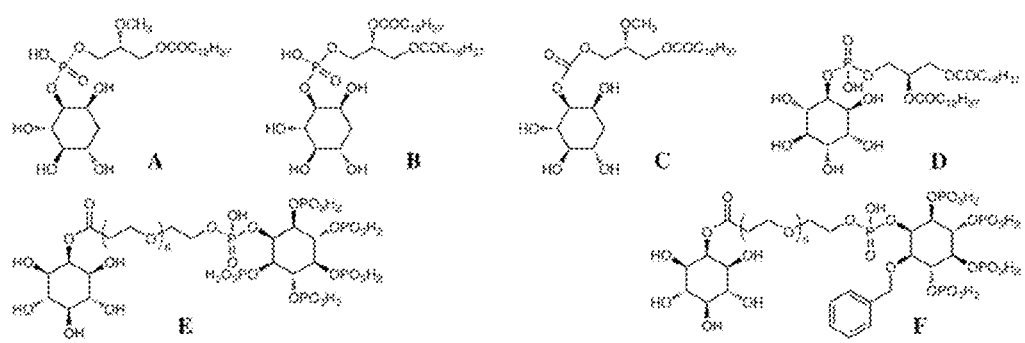
FIG. 1—Examples of inositol structures are provided, in accordance with an embodiment of the present invention.

Described herein are compounds that are selective inhibitors of PI3K isoforms and mutant forms. For example: Class I PI3K-heterodimeric molecules composed of a regulatory and a catalytic subunit, which can be further divided between IA and IB subsets on sequence similarity. Class IA PI3K is composed of a heterodimer between a p110 catalytic subunit and a p85 regulatory subunit. There are five variants of the p85 regulatory subunit, designated as p85α, p55α, p50α, p85β, and p85γ. Variants of the p110 catalytic subunit designated p110α, β, or δ catalytic subunit. The first three regulatory subunits are all splice variants of the same gene (Pik3r1), the other two being expressed by other genes (Pik3r2 and Pik3r3, p85β, and p55γ, respectively). The most expressed regulatory subunit is p85α; all three catalytic subunits are expressed by separate genes (Pik3ca, Pik3cb, and Pik3cd for p110α, p110β, and p110δ, respectively). The first two p110 isoforms (α and β) are expressed in all cells, but p110δ is expressed primarily in leukocytes. The regulatory p110 and catalytic p110γ subunits comprise the type IB PI3K and are encoded by a single gene each.

Class II comprises three catalytic isoforms (C2α, C2β, and C2γ), but, unlike Classes I and III, there are no regulatory proteins. Class II catalyze the production of PIP(3) and PIP2(3,4) from PI; however, little is known about their role in immune cells. C2α and C2β are expressed through the body, however expression of C2γ is limited to hepatocytes. The distinct feature of Class II PI3Ks is the C-terminal C2 domain. This domain lacks critical Asp. residues to coordinate binding of Ca2+, which suggests class II PI3Ks bind lipids in a Ca2+-independent manner Class III produces only PIPS from PI but are more similar to Class I in structure, as they exist as a heterodimers of a catalytic (Vps34) and a regulatory (Vps15/p150) subunits. Fiona M, et al., 2003.

Furthermore, some compounds are inhibitors of Akt and PDK1, mTOR, or bind to Plekstrin Homology Domains (PH) domains. For example, some compounds are up regulators of P53 tumor suppressor and wild type P53 tumor suppressor and down regulators of mutant P53 tumor suppressor. One of the compounds is a KRAS inhibitor which to date no other compound exists to inhibit this particular oncogene. These compounds are expected to be low or non-toxic compounds as compared to many known anti-cancer agents.

Embodiments of the present invention can provide low-toxicity inositol compounds that can inhibit and/or down regulate oncogene KRAS, PI3KT/AKT/PD1/mTOR P53 tumor suppressor mutant form, Up regulators of P53 tumor suppressor and P53 wild type tumor suppressor, and bind pleckstrin homology (PH) domains. In particular, the compounds can selectively inhibit several classes of PI3Kinases and their isoforms, for example (delta, gamma) and one or more of the Akt isoforms.

In an embodiment, a compound can inhibit the KRAS oncogene. In another embodiment, compounds of the present invention can up regulate the P53 tumor suppressor and wild type tumor suppressor. In another embodiment, one or more compounds can inhibit the P53 tumor suppressor mutant form. In another embodiment, compounds of the present invention inhibit PI3K. In another embodiment, one or more compounds can inhibit Akt. In another embodiment, one or more compounds can inhibit PDK1. In another embodiment, one or more compounds can inhibit mTOR. In another embodiment, one or more compounds can bind PH domains. In some embodiments, one or more compounds can inhibit one of PI3K, AKT/mTOR and PDK1. In some embodiments, one or more compounds can inhibit two of PI3K, AKT, and PDK1. In some embodiments, one or more compounds can inhibit all of PI3K, AKT/mTOR and PDK1.

Embodiments of the present invention can also provide methods of inhibiting oncogenic signaling pathways up regulated in solid and wet tumors by administering a compound to a patient in need of treatment for cancer.

The compositions and pharmaceutical formulations described herein can be used with various cancer(s), for example those described by the National Cancer Institute such as lymphoblastic leukemia (ALL), Acute myeloid leukemia, Adrenocortical carcinoma, AIDS-related cancers, AIDS-related lymphoma, Anal cancer, Appendix cancer, Astrocytoma, childhood cerebellar or cerebral, Basal-cell carcinoma, Bile duct cancer, extrahepatic (see Cholangiocarcinoma), Bladder cancer, Bone tumor, Osteosarcoma/Malignant fibrous histiocytoma, Brainstem glioma, Brain cancer, Brain, tumor, cerebellar astrocytoma, Brain tumor, cerebral astrocytoma/malignant glioma, Brain tumor, ependymoma, Brain tumor, medulloblastoma, Brain tumor, supratentorial primitive neuroectodermal tumors, Brain tumor, visual pathway and hypothalamic glioma, Breast cancer, bronchial, adenomas/carcinoids, Burkitt's lymphoma, Carcinoid tumor, Carcinoid tumor, gastrointestinal, Carcinoma of unknown primary, Central nervous system lymphoma, primary Cerebellar astrocytoma, childhood Cerebral astrocytoma/Malignant glioma, childhood, Cervical cancer, Childhood cancers, Chronic lymphocytic leukemia, Chronic myelogenous leukemia, Chronic myeloproliferative disorders, Colon Cancer, Cutaneous T-cell lymphoma, Desmoplastic small round cell tumor, Endometrial cancer, Ependymoma, Esophageal cancer, Ewing's sarcoma in the Ewing family of tumors, Extracranial germ cell tumor, Childhood Extragonadal Germ cell tumor, Extrahepatic bile duct cancer, Eye Cancer, Intraocular melanoma, Eye Cancer, Retinoblastoma, Gallbladder cancer, Gastric (Stomach) cancer, Gastrointestinal Carcinoid Tumor, Gastrointestinal stromal tumor (GIST), Germ cell tumor: extracranial, extragonadal, or ovarian, Gestational trophoblastic tumor, Glioma of the brain stem, Glioma, Childhood Cerebral Astrocytoma, Glioma, Childhood Visual Pathway and Hypothalamic Gastric carcinoid, Hairy cell leukemia, Head and neck cancer, Heart cancer, Hepatocellular (liver) cancer, Hodgkin lymphoma, Hypopharyngeal cancer, Hypothalamic and visual pathway glioma, childhood Intraocular Melanoma, Islet Cell Carcinoma (Endocrine Pancreas), Kaposi sarcoma, Kidney cancer (renal cell cancer), Laryngeal Cancer, Leukemias, Leukemia, acute lymphoblastic (also called acute lymphocytic leukemia), Leukemia, acute myeloid (also called acute myelogenous leukemia), Leukemia, chronic lymphocytic (also called chronic lymphocytic leukemia), Leukemia, chronic myelogenous (also called chronic myeloid leukemia), Leukemia, hairy cell, Lip and Oral Cavity Cancer, Liposarcoma, Liver Cancer (Primary), Lung Cancer, Non-Small Cell, Lung Cancer, Small Cell, Lymphomas, Lymphoma, AIDS-related Lymphoma, Burkitt Lymphoma, cutaneous T-Cell, Lymphoma, Hodgkin Lymphomas, Non-Hodgkin (an old classification of all lymphomas except Hodgkin's) Lymphoma, Primary Central Nervous System, Macroglobulinemia, Waldenström, Malignant Fibrous Histiocytoma of Bone/Osteosarcoma, medulloblastoma, Childhood Melanoma, Melanoma, Intraocular (Eye), Merkel Cell Carcinoma, Mesothelioma, Adult Malignant, Mesothelioma, Childhood, Metastatic Squamous Neck Cancer with Occult Primary, Mouth Cancer, Multiple Endocrine Neoplasia Syndrome, Childhood Multiple Myeloma/Plasma Cell Neoplasm, Mycosis Fungoides, Myelodysplastic Syndromes, myelodysplastic/Myeloproliferative Diseases, Myelogenous Leukemia, Chronic Myeloid Leukemia, Adult Acute, Myeloid Leukemia, Childhood Acute, Myeloma, Multiple (Cancer of the Bone-Marrow), Myeloproliferative Disorders, Chronic, Nasal cavity and paranasal sinus cancer, Nasopharyngeal carcinoma, Neuroblastoma, Non-Hodgkin lymphoma, Non-small cell lung cancer, Oral Cancer, Oropharyngeal cancer, Osteosarcoma/malignant fibrous histiocytoma of bone, Ovarian cancer, Ovarian epithelial cancer (Surface epithelial-stromal tumor), Ovarian germ cell tumor, Ovarian low malignant potential tumor, Pancreatic cancer, Pancreatic cancer, islet cell, Paranasal sinus and nasal cavity cancer, Parathyroid cancer, Penile cancer, Pharyngeal cancer, Pheochromocytoma, Pineal astrocytoma, Pineal, germinoma, Pineoblastoma and supratentorial primitive neuroectodermal tumors, childhood, Pituitary adenoma, Plasma cell neoplasia/Multiple myeloma, Pleuropulmonary blastoma, Primary central nervous system lymphoma, Prostate cancer, Rectal cancer, Renal cell carcinoma (kidney cancer), Renal pelvis and ureter, transitional cell cancer, Retinoblastoma, Rhabdomyosarcoma, childhood, Salivary gland cancer, Sarcoma, Ewing family of tumors, Sarcoma, Kaposi, Sarcoma, soft tissue, Sarcoma, uterine, Sézary syndrome, Skin cancer (nonmelanoma, Skin cancer (melanoma), Skin carcinoma, Merkel cell, Small cell lung cancer, Small intestine cancer, Soft tissue sarcoma, Squamous cell carcinoma—see Skin cancer (nonmelanoma), Squamous neck cancer with occult primary, metastatic Stomach cancer, Supratentorial primitive neuroectodermal tumor, childhood, T-Cell lymphoma, cutaneous—see Mycosis Fungoides and Sézary syndrome, Testicular cancer, Throat cancer, Thymoma, childhood Thymoma and Thymic carcinoma, Thyroid cancer, Thyroid cancer, childhood, Transitional cell cancer of the renal pelvis and ureter, Trophoblastic tumor, gestational, Unknown primary site, carcinoma of, adult, Unknown primary site, cancer of, childhood, Ureter and renal pelvis, transitional cell cancer, Urethral cancer, Uterine cancer, endometrial, Uterine sarcoma, Vaginal cancer, Visual pathway and hypothalamic glioma, childhood, Vulvar cancer, Waldenström macroglobulinemia, Wilms tumor (kidney cancer), childhood.

In various embodiments, the compounds can be of formula I:

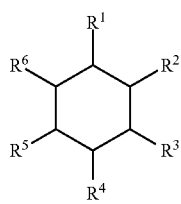

wherein:

one of $R^1$-$R^6$ is —O—Y and five of $R^1$-$R^6$ are OH, or one of $R^1$-$R^6$ is —O—Y, four of $R^1$-$R^6$ are OH and one of $R^1$-$R^6$ is H;

each of $R^1$-$R^6$ may be independently in an axial or an equatorial orientation;

Y is selected from —P(=O)(—OH)—OR$^7$, —C(=O)—OR$^7$, and —C(=O)—R$^8$;

$R^7$ is —CH$_2$—CH(OR$^9$)CH$_2$OR$^{10}$;

$R^8$ is —(CH$_2$CH$_2$O—)$_x$—CH$_2$CH$_2$—Z;

$R^9$ and $R^{10}$ are independently selected from a $C_1$-$C_6$ alkyl group and a $C_6$-$C_{26}$ acyl group optionally possessing 0-4 double bonds, triple bonds or a combination thereof;

each double bond of $R^9$ and $R^{10}$ may be independently in a cis or a trans orientation; and x is an integer from 1-6;

Z is a structure of formula II:

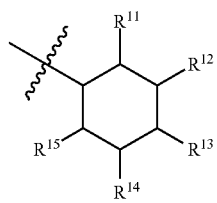

wherein:

each of four of $R^{11}$ through $R^{15}$ is —O—P(=O)(OH)$_2$;

one of $R^{11}$ through $R^{15}$ is selected from benzyloxy and —O—P(=O)(OH)$_2$; and each of substituent on the ring of formula II may be independently in either an axial or an equatorial orientation.

In various embodiments, the compounds can include those of formula I:

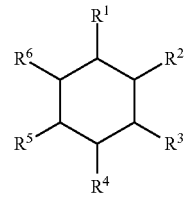

wherein:

one of $R^1$-$R^6$ is —O—Y and five of $R^1$-$R^6$ are OH;

each of $R^1$-$R^6$ may be independently in an axial or an equatorial orientation;

Y is —C(=O)—R$^8$;

$R^8$ is —(CH$_2$CH$_2$O—)$_x$—CH$_2$CH$_2$—Z;

x is an integer from 1-6;

Z is a structure of formula II:

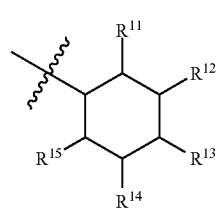

wherein:

each of four of $R^{11}$ through $R^{15}$ is —O—P(=O)(OH)$_2$;

one of $R^{11}$ through $R^{15}$ is selected from benzyloxy and —O—P(=O)(OH)$_2$; and each of substituent on the ring of formula II may be independently in either an axial or an equatorial orientation.

In various embodiments, the compounds can include those of formula XI:

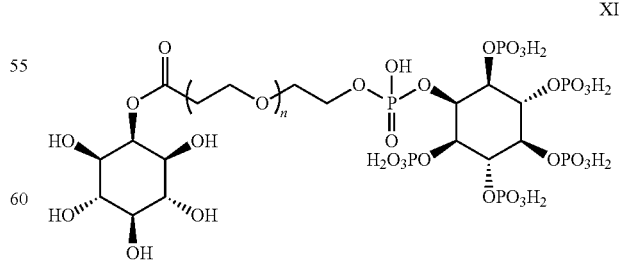

wherein n is an integer from 1-6.

In various embodiments, the compounds can include those of formula XII:

XII

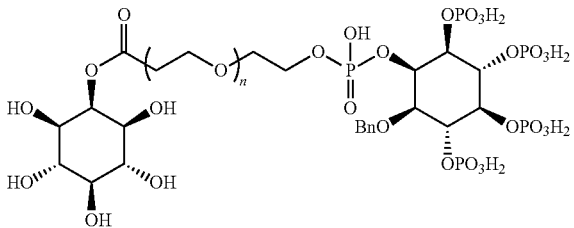

wherein n is an integer from 1-6.

In various embodiments, the compounds can include those of formula I:

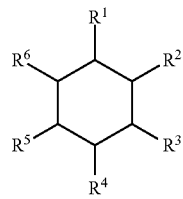

I wherein:
one of $R^1$-$R^6$ is —O—Y and five of $R^1$-$R^6$ are OH, or one of $R^1$-$R^6$ is —O—Y, four of $R^1$-$R^6$ are OH and one of $R^1$-$R^6$ is H;
each of $R^1$-$R^6$ may be independently in an axial or an equatorial orientation;
Y is selected from —P(=O)(—OH)—$OR^7$ and —C(=O)—$OR^7$;
$R^7$ is —$CH_2$—CH($OR^9$)$CH_2OR^{10}$;
$R^9$ and $R^{10}$ are independently selected from a $C_1$-$C_6$ alkyl group and a $C_6$-$C_{26}$ acyl group optionally possessing 0-4 double bonds, triple bonds or a combination thereof; and
each double bond of $R^9$ and $R^{10}$ may be independently in a cis or a trans orientation.

In various embodiments, the compounds can include those of formula I:

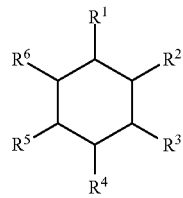

I wherein:
one of $R^1$-$R^6$ is —O—Y, four of $R^1$-$R^6$ are OH and one of $R^1$-$R^6$ is H;
each of $R^1$-$R^6$ may be independently in an axial or an equatorial orientation;
Y is selected from —P(=O)(—OH)—$OR^7$ and —C(=O)—$OR^7$;
$R^7$ is —$CH_2$—CH($OR^9$)$CH_2OR^{10}$;
$R^9$ and $R^{10}$ are independently selected from a $C_1$-$C_6$ alkyl group and a $C_6$-$C_{26}$ acyl group optionally possessing 0-4 double bonds, triple bonds or a combination thereof; and
each double bond of $R^9$ and $R^{10}$ may be independently in a cis or a trans orientation.

In various embodiments, the compounds can include those of formula XIII:

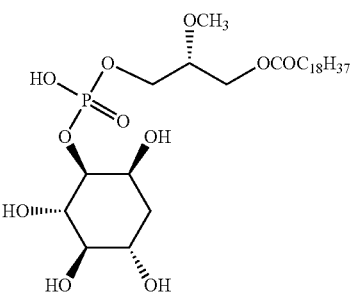

XIII

In various embodiments, the compounds can include those of formula XIV:

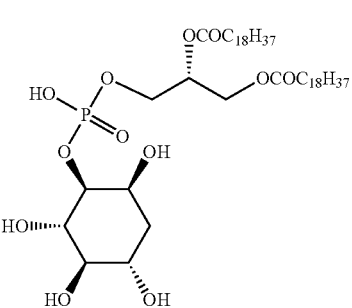

XIV

In various embodiments, the compounds can include those of formula XV:

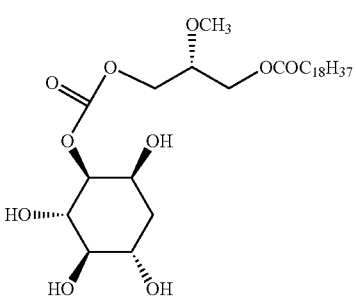

XV

In various embodiments, the compounds can include those of formula I:

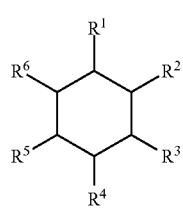

I wherein:
one of $R^1$-$R^6$ is —O—Y and five of $R^1$-$R^6$ are OH;
each of $R^1$-$R^6$ may be independently in an axial or an equatorial orientation;
Y is selected from —P(=O)(—OH)—$OR^7$ and —C(=O)—$OR^7$;
$R^7$ is —$CH_2$—CH($OR^9$)$CH_2OR^{10}$;
$R^9$ and $R^{10}$ are independently selected from a $C_1$-$C_6$ alkyl group and a $C_6$-$C_{26}$ acyl group optionally possessing 0-4 double bonds, triple bonds or a combination thereof; and
each double bond of $R^9$ and $R^{10}$ may be independently in a cis or a trans orientation.

In various embodiments, the compounds can include those of formula XVI:

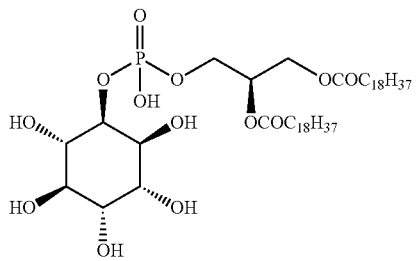

XVI

In one or more embodiments, a compound of formula IV can be used for the preparation of compounds of formula I, where formula IV is:

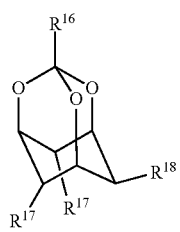

IV wherein:
$R^{16}$ is H, $C_1$-$C_6$ alkyl or phenyl;
each $R^{17}$ is —O-benzyl, —O-TMS, —O-TBDMS, —O-TBDPS, —O-(4-methoxybenzyl), acetoxy or —O-MOM;
$R^{18}$ is OH; and
each $R^{17}$ and $R^{18}$ may be independently in an axial or an equatorial orientation.

In an embodiment, the compound can be formula IV:

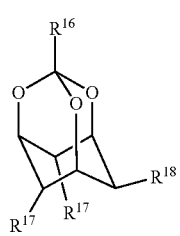

IV wherein:
$R^{16}$ is phenyl;
Each $R^{17}$ is —O-benzyl;
$R^{18}$ is OH;
each $R^{17}$ is in an axial orientation; and
$R^{18}$ is in an equatorial orientation.

In one or more embodiments, a compound of formula VI can be used for the preparation of compounds of formula I, where formula VI is:

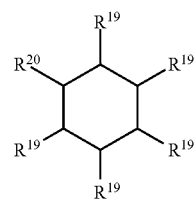

VI wherein:
each $R^{19}$ is —OP(O)($OBn$)$_2$;
$R^{20}$ is OH; and
each of $R^{19}$ and $R^{20}$ may be independently in an axial or an equatorial orientation.

In one or more embodiments, a compound of formula IX can be used for the preparation of compounds of formula I, where formula IX is:

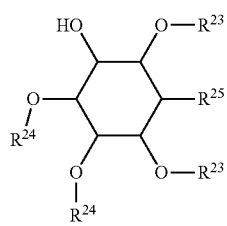

IX wherein:
each $R^{23}$ is independently selected from benzyl, TBDMS, 4-methoxybenzyl and MOM;
each $R^{24}$ is MOM or each $R^{24}$ is covalently linked to one another forming a di-acetal protecting group;
$R^{25}$ is H, —O-MOM, —O-benzyl, —OTBDMS, or —O-(4-methoxybenzyl); and all ring substituents may be independently in an axial or an equatorial orientation.

In various embodiments, the compound can be formula IX:

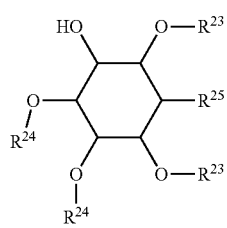

IX wherein:
each $R^{23}$ is independently selected from benzyl and MOM;
each $R^{24}$ is MOM or each $R^{24}$ is covalently linked to one another forming a di-acetal protecting group;

$R^{25}$ is selected from H and —O-MOM; and all ring substituents may be independently in an axial or an equatorial orientation.

In an embodiment, the compound can be formula IX:

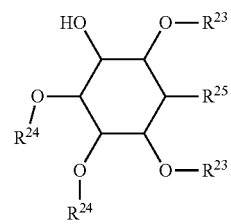

IX wherein:

each $R^{23}$ is benzyl;

each $R^{24}$ is covalently linked to one another forming a di-acetal protecting group;

$R^{25}$ is H; and all ring substituents may be independently in an axial or an equatorial orientation.

In an embodiment, the compound can be formula IX:

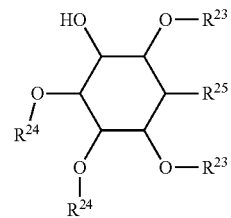

IX wherein:

each $R^{23}$ is MOM;

each $R^{24}$ is MOM;

$R^{25}$—O-MOM; and all ring substituents may be independently in an axial or an equatorial orientation.

Of the compounds of the various embodiments, compounds having the ring structure shown as structure I are of Myo-inoisitol, D-chiro-inositol, Scyllo-inositol, Muco-inositol, Neo-inositol, Allo-inositol, Epi-inositol, Cis-inositol, L-chiroinositol orientation. In various embodiments, compounds having the ring structure shown as structure I are the Myo-inositol or D-chiro-inositol orientation. The ring shown as structure II are of the myo-inositol, D-Chiro-inositol, Scyllo-inositol, Muco-inositol, Neo-inositol, Allo-inositol, Epi-inositol, Cis-inositol, L-chiroinositol, more preferably, the Myo-inositol or D-Chiro-inositol orientation. In various embodiments, both the rings shown as structure I and structure II are of Myo-inoisitol, D-chiro-inositol, Scyllo-inositol, Muco-inositol, Neo-inositol, Allo-inositol, Epi-inositol, Cis-inositol, L-chiroinositol. In various embodiments, compounds having the ring structure shown as structure I and structure II can be myo-inositol or D-chiro-inositol orientation.

In various embodiments, a method is provided for producing compounds that include those of formula I:

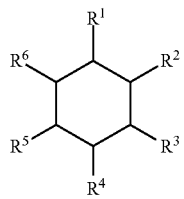

I comprising the steps of:

(a) reacting a compound of formula III with a compound of formula IV producing a compound of formula V;

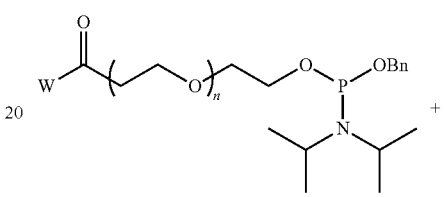

III

IV

V (b) reacting a compound of formula V with a compound of formula VI producing a compound of formula VII;

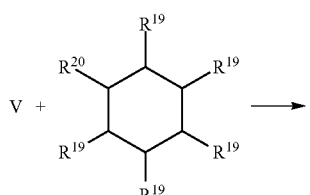

VI

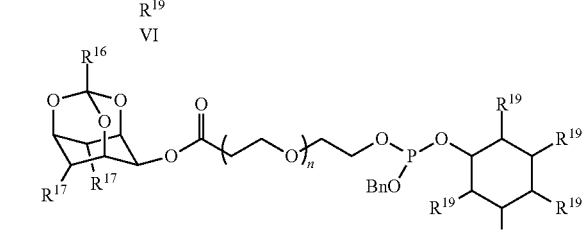

VII (c) oxidizing a phosphite to a phosphate; and
(d) cleaving all protecting groups,
wherein:
one of $R^1$-$R^6$ is —O—Y and five of $R^1$-$R^6$ are OH;
each of $R^1$-$R^6$ may be independently in an axial or an equatorial orientation;
Y is —C(=O)—$R^8$;
$R^8$ is —(CH$_2$CH$_2$O—)$_x$—CH$_2$CH$_2$—Z;
x is an integer from 1-6;
Z is a structure of formula II:

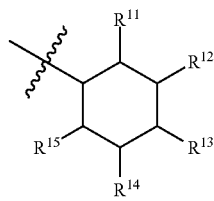

wherein:
each of four of $R^{11}$ through $R^{15}$ is —O—P(=O)(OH)$_2$;
one of $R^{11}$ through $R^{15}$ is selected from benzyloxy and —O—P(=O)(OH)$_2$;
each of substituent on the ring of formula II may be independently in either an axial or an equatorial orientation.
W is a leaving group selected from NHS, 4-nitrophenol, imidazole, HOBT and halide;
$R^{16}$ is H, $C_1$-$C_6$ alkyl or phenyl;
each $R^{17}$ is —O-benzyl, —O-TMS, —O-TBDMS, —O-TBDPS, —O-(4-methoxybenzyl), acetoxy or —O-MOM;
$R^{18}$ is OH;
each $R^{19}$ is —OP(O)(OBn)$_2$;
$R^{20}$ is OH;
each of $R^{17}$, $R^{18}$, $R^{19}$ and $R^{20}$ may be independently in an axial or an equatorial orientation;
protecting groups are independently selected from benzyl ether, benzyl ester, benzyl phosphate, orthobenzoate, orthoformate, TBDMS, and MOM; and
n is an integer from 1-6.

In various embodiments, acylating agents of formula III can react with alcohols of formula IV. Such reactions proceed in the presence of and in the absence of basic acyl transfer catalysts. In various embodiments, the reaction of an acylating agent of formula III with an alcohol of formula IV proceeds spontaneously in solution. In other embodiments, the reaction of an acylating agent of formula III with an alcohol of formula IV proceeds in the presence of a basic acyl transfer catalyst such as N,N-4-dimethylaminopyridine (DMAP), pyridine, imidazole, triazole and tetrazole. Basic acyl transfer catalysts other than DMAP, pyridine, imidazole, triazole and tetrazole may also be used.

In various embodiments, phosphoramidites of formula VI can react with alcohols of formula V in the presence of bases. Such bases include, but are not limited to tetrazole, triazole, imidazole, triethylamine, diisopropyl ethylamine and 1,8-diazabicyclo[5.4.0]undec-7-ene (DBU). One skilled in the art will recognize that bases other than tetrazole, triazole, imidazole, triethylamine, diisopropyl ethylamine and DBU can be used.

One of ordinary skill in the art will recognize that phosphites of formula VII readily oxidize to phosphates in the presence of oxidizing agents. Such oxidizing agents include, but are not limited to hydrogen peroxide, meta-chloroperoxybenzoic acid (mCPBA), tetrabutylammonium periodate and sodium periodate. Oxidizing agents other than hydrogen peroxide, mCPBA, tetrabutylammonium periodate and sodium periodate may also be used.

In various embodiments, different protecting groups compatible with the compounds of the present invention can be used. In the case of inositols, there are many protecting groups for alcohols that protect single hydroxyl groups as well as multiple hydroxyl groups simultaneously. Such protecting groups include, but are not limited to benzyl, 4-methoxybenzyl, TBDMS, TBDPS, TMS, MOM, orthobenzoate, butanedione dimethyl acetal (BDA acetal), acetyl, benzoyl and 4-nitrobenzoyl. Additional protecting groups are also useful. Furthermore, different protecting groups can be simultaneously cleaved utilizing a single reaction. For example, benzyl, 4-methoxybenzyl and orthobenzoate can all be cleaved utilizing catalytic hydrogenation. Additionally, TBDMS, TBDPS, TMS, MOM, orthobenzoate and butanedione dimethyl acetal (BDA acetal) can all be cleaved utilizing acidic hydrolytic conditions. Furthermore, acetyl, benzoyl and 4-nitrobenzoyl can all be cleaved utilizing basic hydrolytic conditions.

In various embodiments, a method is provided for producing compounds that include those of formula I:

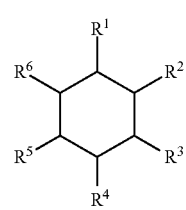

comprising the steps of:
(a) reacting a compound of formula VIII with a compound of formula IX producing a compound of formula X;

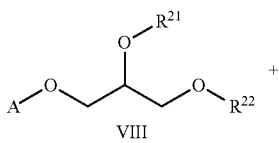

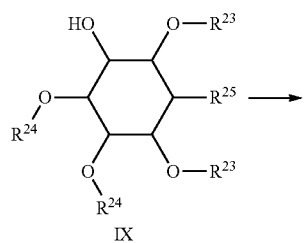

-continued

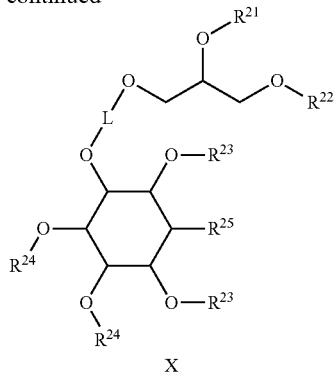

X (b) optionally oxidizing a phosphite to a phosphate; and
(c) cleaving all protecting groups,
wherein:
one of $R^1$-$R^6$ is —O—Y and five of $R^1$-$R^6$ are OH, or one of $R^1$-$R^6$ is —O—Y, four of $R^1$-$R^6$ are OH and one of $R^1$-$R^6$ is H;
each of $R^1$-$R^6$ may be independently in an axial or an equatorial orientation;
Y is selected from —P(=O)(—OH)—$OR^7$ and —C(=O)—$OR^7$;
$R^7$ is —$CH_2$—CH($OR^9$)$CH_2OR^{10}$;
$R^9$ and $R^{10}$ are independently selected from a $C_1$-$C_6$ alkyl group and a $C_6$-$C_{26}$ acyl group optionally possessing 0-4 double bonds, triple bonds or a combination thereof;
each double bond of $R^9$ and $R^{10}$ may be independently in a cis or a trans orientation;
$R^{21}$ and $R^{22}$ are independently selected from a $C_1$-$C_6$ alkyl group and a $C_6$-$C_{26}$ acyl group optionally possessing 0-4 double bonds, triple bonds or a combination thereof;
each $R^{23}$ is independently selected from benzyl, TBDMS, 4-methoxybenzyl and MOM;
each $R^{24}$ is MOM or each $R^{24}$ is covalently linked to one another forming a di-acetal protecting group;
$R^{25}$ is H, —O-MOM, —O-benzyl, —OTBDMS, or —O-(4-methoxybenzyl);
A is

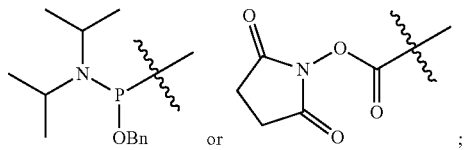 [SMILES: *P(OCc1ccccc1)N(C(C)C)C(C)C ; *C(=O)ON1C(=O)CCC1=O]

L is C=O or P—OBn;
protecting groups are independently selected from benzyl ether, benzyl ester, benzyl phosphate, orthobenzoate, orthoformate, TBDMS, butanedione dimethyl acetal (BDA acetal) and MOM; and
all ring substituents may be independently in an axial or an equatorial orientation.

In various embodiments, when A of formula VIII constitutes a phosphoramidite, a phosphoramidite of formula VIII will react with alcohols of formula IX in the presence of bases. Such bases include, but are not limited to tetrazole, triazole, imidazole, triethylamine, diisopropyl ethylamine and DBU. Bases other than tetrazole, triazole, imidazole, triethylamine, diisopropyl ethylamine and DBU can also be used.

In various embodiments, when A of formula VIII constitutes an N-hydroxysuccinimidyl (NHS) carbonate, an NHS carbonate of formula VIII will react with alcohols of formula IX in the presence of and in the absence of basic acyl transfer catalysts. In certain embodiments, the reaction of an NHS carbonate of formula VIII with an alcohol of formula IX proceeds spontaneously in solution. In other embodiments, the reaction of an NHS carbonate of formula VIII with an alcohol of formula IX proceeds in the presence of a basic acyl transfer catalyst such as DMAP, pyridine, imidazole, triazole and tetrazole. Basic acyl transfer catalysts other than DMAP, pyridine, imidazole, triazole and tetrazole may also be used.

In various embodiments, when L of formula X constitutes a phosphite, phosphites of formula X can readily oxidize to phosphates in the presence of oxidizing agents. Such oxidizing agents include, but are not limited to hydrogen peroxide, mCPBA, tetrabutylammonium periodate and sodium periodate. Oxidizing agents other than hydrogen peroxide, mCPBA, tetrabutylammonium periodate and sodium periodate may also be used.

In various embodiments, when L of formula X constitutes a carbonate, no step involving oxidation of a phosphite to a phosphate is required.

There are many protecting groups compatible with the compounds of the present invention. In the case of inositols, there are many protecting groups for alcohols that protect single hydroxyl groups as well as multiple hydroxyl groups simultaneously. Such protecting groups include, but are not limited to benzyl, 4-methoxybenzyl, TBDMS, TBDPS, TMS, MOM, orthobenzoate, butanedione dimethyl acetal (BDA acetal), acetyl, benzoyl and 4-nitrobenzoyl. Additional protecting groups are also useful. Furthermore, different protecting groups can be simultaneously cleaved utilizing a single reaction. For example, benzyl, 4-methoxybenzyl and orthobenzoate can all be cleaved utilizing catalytic hydrogenation. Additionally, TBDMS, TBDPS, TMS, MOM, orthobenzoate and butanedione dimethyl acetal (BDA acetal) can all be cleaved utilizing acidic hydrolytic conditions. Furthermore, acetyl, benzoyl and 4-nitrobenzoyl can all be cleaved utilizing basic hydrolytic conditions.

In one or more embodiments, compounds of the present invention in particular compounds of Formula I (including, without limitation, compounds of Formulae A-F, VI, XI-XVI, 12, 35, 37, 40, and 56) can be administered alone or in a pharmaceutical formulation. In one or more embodiments, compounds described herein are formulated with one or more pharmaceutically acceptable carriers, adjuvants, excipients, diluents, fillers, buffers, stabilizers, preservatives, lubricants, or other materials and optionally other therapeutic or prophylactic agents.

Accordingly, the embodiments provide a pharmaceutical composition comprising at least one compound including compounds of Formula I (e.g., without limitation, compounds of Formulae A-F, VI, XI-XVI, 12, 35, 37, 40, and 56). The methods described herein include administration of one or more pharmaceutical compositions, as discussed herein, in which a compound described herein is admixed together with one or more pharmaceutically acceptable carriers, excipients, buffers, adjuvants, stabilizers, or other materials, as described herein.

Suitable carriers, excipients, etc. can be found in standard pharmaceutical texts, for example, Remington's Pharmaceutical Sciences, 18th edition, Mack Publishing Company, Easton, Pa., 1990. The pharmaceutical compositions may conveniently be presented in unit dosage form and may be prepared by any methods known in the art of pharmacy. Such methods include bringing into association the active compound(s) with the carrier which constitutes one or more accessory ingredients. In general, the pharmaceutical compositions are prepared by uniformly and intimately bringing into association the active compound with a liquid carriers or finely divided solid carriers or both, and then if necessary shaping the product.

In various embodiments, the pharmaceutical compositions may be in the form of liquids, solutions, suspensions, aerosols, inhalers, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Pharmaceutical compositions suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by, for example, compression or molding, where one or more accessory ingredients can be included. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

In one or more embodiments, pharmaceutical compositions suitable for parenteral administration (e.g. by injection, including cutaneous, subcutaneous, intramuscular, intravenous and intradermal), include aqueous and nonaqueous isotonic, pyrogen-free, sterile injection solutions which may contain buffers, preservatives, stabilizers, bacteriostats, and solutes which render the pharmaceutical composition isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such pharmaceutical compositions include Sodium Chloride Injection, Ringer's Solution, or Lactated Ringer's Injection. The pharmaceutical compositions may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Pharmaceutical compositions may be in the form of liposomes or other microparticulate systems which are designed to target the active compound to blood components or one or more organs.

In one or more embodiments, pharmaceutical compositions suitable for topical administration (e.g. transdermal, intranasal, ocular, buccal, and sublingual) may be formulated as an ointment, cream, suspension, lotion, powder, solution, past, gel, spray, aerosol, or oil. Alternatively, a pharmaceutical composition may comprise a patch or a dressing such as a bandage or adhesive plaster impregnated with active compounds and optionally one or more excipients or diluents.

In one or more embodiments, pharmaceutical compositions suitable for topical administration in the mouth include lozenges comprising the active compound in a flavored basis, usually sucrose and acacia or tragacanth; pastilles comprising the active compound in an inert basis such as gelatin and glycerin, or sucrose and acacia; and mouth-washes comprising the active compound in a suitable liquid carrier.

In one or more embodiments, pharmaceutical compositions suitable for topical administration to the eye also include eye drops wherein the active compound is dissolved or suspended in a suitable carrier, especially an aqueous solvent for the active compound.

In one or more embodiments, pharmaceutical compositions suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable pharmaceutical compositions wherein the carrier is a liquid for administration as, for example, nasal spray, nasal drops, or by aerosol administration by nebulizer, include aqueous or oily solutions of the active compound.

In one or more embodiments, pharmaceutical compositions suitable for administration by inhalation include those presented as an aerosol spray from a pressurized pack, with the use of a suitable propellant, such as dichlorodifluoromethane, trichlorofluoromethane, dichloro-tetrafluoroethane, carbon dioxide, or other suitable gases. Further pharmaceutical compositions suitable for inhalation include those presented as a nebulizer.

In one or more embodiments, pharmaceutical compositions suitable for topical administration via the skin include ointments, creams, and emulsions. When formulated in an ointment, the active compound may be employed with either a paraffinic or a water-miscible ointment base. In various embodiments, the active compounds may be formulated in a cream with an oil-in-water cream base. The aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol. The topical pharmaceutical compositions may include a compound which enhances absorption or penetration of the active compound through the skin or other affected areas. Examples of such dermal penetration enhancers include dimethylsulfoxide (DMSO) and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. A hydrophilic emulsifier can be included together with a lipophilic emulsifier which acts as a stabilizer. In various embodiments, both an oil and a fat can be included. Together, the emulsifier(s) with or without stabilizer(s) make up the so-called emulsifying wax, and the emulsifying wax together with the oil and/or fat make up the so-called emulsifying ointment base which forms the oily dispersed phase of the cream pharmaceutical compositions.

Suitable emulgents and emulsion stabilizers include, for example, Tween 60, Span 80, cetostearyl alcohol, myristyl alcohol, glyceryl monostearate and sodium lauryl sulfate. The choice of suitable oils or fats for the pharmaceutical composition is based on achieving the desired cosmetic properties, since the solubility of the active compound in most oils likely to be used in pharmaceutical emulsion pharmaceutical compositions may be very low. Thus the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

In one or more embodiments, pharmaceutical compositions suitable for rectal administration may be presented as a suppository with a suitable base comprising, for example, cocoa butter or a salicylate.

In one or more embodiments, pharmaceutical compositions suitable for vaginal administration may be presented as pessaries, tampons, creams, gels, pastes, foams or spray pharmaceutical compositions containing in addition to the active compound, such carriers as are known in the art to be appropriate.

It will be appreciated that appropriate dosages of the compounds and compositions comprising the active compounds, can vary from patient to patient. Determining the optimal dosage will generally involve the balancing of the level of therapeutic benefit against any risk or deleterious side effects of the treatments described herein. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be affected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound may be in the range of about 100 ug to about 250 mg per kilogram body weight of the subject per day. Exemplary, non-limiting dosing schedules follow.

Compounds of Formula I in which Y is —C(=O)R$^9$ (i.e., those having an ethylene glycol bridge) can be administered to adults and children (a) in a range of 1.5-9 grams divided into 2 oral daily doses or (b) at a dose of about 40 mg/m$^2$ for every 4 weeks for an overall dose intensity of about 10 mg/m$^2$ per week, or (c) biweekly at a dose of about 15 mg/m$^2$ for four administrations.

For compounds of Formula I in which Y is either —P(=O)(—OH)(—OR$^7$ or —C(=O)—)R$^7$, the compounds can be administered at an initial dose of 40-50 mg/kg given intravenously in divided doses over a period of 2-5 days, or alternatively 10-15 mg/kg can be given every 7-10 days or 3-5 mg/kg twice weekly. Oral administration dosing is typically in the range of 1-5 mg/kg/day for both initial and maintenance dosing.

In the compounds of formula I, the compounds comprise anti-cancer agents. In the course of treating a patient in need of a cancer therapy, compounds of the present invention may be administered with one or more exemplary anti-cancer/chemotherapeutic agents.

Exemplary anti-cancer/chemotherapeutic agents for us in combination with the present invention compounds or for use in combination formulations of the present invention, include, but are not limited to, the following:

alkylating agents (including, without limitation): nitrogen mustards, ethylenimine derivatives, alkyl sulfonates, nitrosoureas and triazenes): uracil mustard (Aminouracil-Mustard®, Chlorethaminacil®, Demethyldopan®, Desmethyldopan®, Haemanthamine®, Nordopan®, Uracilnitrogen Mustard®, Uracillost®, Uracilmostaza®, Uramustin®, Uramustine®), bendamustine (Treakisym®, Ribomustin®, Treanda®) chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexylen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), estramustine (Emcyt®, Estracit®), fotemustine, irofulven, mannosulfan, mitobronitol, nimustine, procarbazine, ranimustine, semustine, triaziquone, treosulfan, and Dacarbazine (DTIC-Dome®).

anti-EGFR antibodies (including, without limitation): (e.g., cetuximab (Erbitux®), panitumumab (Vectibix®), and gefitinib (Iressa®).

anti-Her-2 antibodies (including, without limitation): (e.g., trastuzumab (Herceptin®) and other antibodies from Genentech).

antimetabolites (including, without limitation), folic acid antagonists (also referred to herein as antifolates), pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), carmofur, cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), mercaptopurine (Puri-Nethol®), capecitabine (Xeloda®), nelarabine (Arranon®), azacitidine (Vidaza®), decitabine (Dacogen®), enocitabine (Sunrabin®), sapacitabine, tegafur-uracil, tiazofurine, tioguanine, trofosfamide, and gemcitabine (Gemzar®).

vinca alkaloids (including, without limitation): vinblastine (Velban®, Velsar®), vincristine (Vincasar®, Oncovin®), vindesine (Eldisine®), vinorelbine (Navelbine®), vinflunine (Javlor®). platinum-based agents: carboplatin (Paraplat®, Paraplatin®), cisplatin (Platinol®), oxaliplatin (Eloxatin®), nedaplatin, satraplatin, triplatin.

anthracyclines: daunorubicin (Cerubidine®, Rubidomycin®), doxorubicin (Adriamycin®), epirubicin (Ellence®), idarubicin (Idamycin®), mitoxantrone (Novantrone®), valrubicin (Valstar®), aclarubicin, amrubicin, liposomal doxorubicin, liposomal daunorubicin, pirarubicin, pixantrone, zorubicin.

topoisomerase inhibitors (including, without limitation): topotecan (Hycamtin®), irinotecan (Camptosar®), etoposide (Toposar®, VePesid®), teniposide (Vumon®), lamellarin D, SN-38, camptothecin (e.g., IT-101), belotecan, rubitecan.

Taxanes (including, without limitation): paclitaxel (Taxol®), docetaxel (Taxotere®), larotaxel, cabazitaxel, ortataxel, tesetaxel.

Antibiotics (including, without limitation): actinomycin (Cosmegen®), bleomycin (Blenoxane®), hydroxyurea (Droxia®, Hydrea®), mitomycin (Mitozytrex®, Mutamycin®).

Immunomodulators (including, without limitation): lenalidomide (Revlimid®), thalidomide (Thalomid®).

immune cell antibodies (including, without limitation): alemtuzamab (Campath®), gemtuzumab (Myelotarg®), rituximab (Rituxan®), tositumomab (Bexxar®)

interferons (including, without limitation), (e.g., IFN-alpha (Alferon®, Roferon-A®, Intron®-A) or IFN-gamma (Actimmune®)).

Interleukins (including, without limitation): IL-1, IL-2 (Proleukin®), IL-24, IL-6 (Sigosix®), IL-12.

HSP90 inhibitors (including, without limitation), (e.g., geldanamycin or any of its derivatives). In certain embodiments, the HSP90 inhibitor is selected from geldanamycin, 17-alkylamino-17-desmethoxygeldanamycin ("17-AAG") or 17-(2-dimethylaminoethyl)amino-17-desmethoxygeldanamycin ("17-DMAG").

anti-androgens, which include, without limitation nilutamide (Nilandron®) and bicalutamide (Caxodex®).

antiestrogens which include, without limitation tamoxifen (Nolvadex®), toremifene (Fareston®), letrozole (Femara®), testolactone (Teslac®), anastrozole (Arimidex®), bicalutamide (Casodex®), exemestane (Aromasin®), flutamide (Eulexin®), fulvestrant (Faslodex®), raloxifene (Evista®, Keoxifene®) and raloxifene hydrochloride.

anti-hypercalcaemia (including, without limitation), agents which include without limitation gallium (III) nitrate hydrate (Ganite®) and pamidronate disodium (Aredia®).

Apoptosis inducers which include without limitation ethanol, 2-[[3-(2,3-dichlorophenoxy)propyl]amino]-(9Cl), gambogic acid, elesclomol, embelin and arsenic trioxide (Trisenox®).

Aurora kinase inhibitors which include without limitation binucleine 2.

Bruton's tyrosine kinase inhibitors which include without limitation terreic acid.

calcineurin inhibitors which include without limitation cypermethrin, deltamethrin, fenvalerate and tyrphostin 8.

CaM kinase II inhibitors which include without limitation 5-Isoquinolinesulfonic acid, 4-[{2S}-2-[(5-isoquinolinylsulfonyl)methylamino]-3-oxo-3-{4-phenyl-1-pipe-razinyl)propyl]phenyl ester and benzenesulfonamide.

CD45 tyrosine phosphatase inhibitors which include without limitation phosphonic acid.

CDC25 phosphatase inhibitors which include without limitation 1,4-naphthalene dione, 2,3-bis R2-hydroxyethyl) thiol-(9Cl).

CHK kinase inhibitors which include without limitation debromohymenialdisine.

cyclooxygenase inhibitors which include without limitation 1H-indole-3-acetamide, 1-(4-chlorobenzoyl)-5-methoxy-2-methyl-N-(2-phenylethyl)-(9Cl), 5-alkyl substituted 2-arylaminophenylacetic acid and its derivatives (e.g., celecoxib (Celebrex®), rofecoxib (Vioxx®), etoricoxib (Arcoxia®), lumiracoxib (Prexige®), valdecoxib (Bextra®) or 5-alkyl-2-arylaminophenylacetic acid).

cRAF kinase inhibitors which include without limitation 3-(3,5-dibromo-4-hydroxybenzylidene)-5-iodo-1,3-dihydroindol-2-one and benzamide, 3-(dimethylamino)-N-[3-[(4-hydroxybenzoyl)amino]-4-methylphenyl]-(9Cl).

cyclin dependent kinase inhibitors which include without limitation olomoucine and its derivatives, purvalanol B, roascovitine (Seliciclib®), indirubin, kenpaullone, purvalanol A and indirubin-3'-monooxime.

cysteine protease inhibitors which include without limitation 4-morpholinecarboxamide, N-[(1S)-3-fluoro-2-oxo-1-(2-phenylethyl)propyl]amino]-2-oxo-1-(phenylmeth-yl) ethyl]-(9Cl).

DNA intercalators which include without limitation plicamycin (Mithracin®) and daptomycin (Cubicin®).

DNA strand breakers which include without limitation bleomycin (Blenoxane®).

E3 ligase inhibitors which include without limitation N-((3,3,3-trifluoro-2-trifluoromethyl)propionyl)sulfanilamide.

EGF Pathway Inhibitors which include, without limitation tyrphostin 46, EKB-569, erlotinib (Tarceva®), gefitinib (Iressa®), lapatinib (Tykerb®) and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980.

farnesyltransferase inhibitors which include without limitation ahydroxyfarnesylphosphonic acid, butanoic acid, 2-[(2S)-2-[[(2S,3S)-2-[[(2R)-2-amino-3-mercaptopropyl] amino]-3-methylpent-yl]oxy]-1-oxo-3-phenylpropyl] amino]-4-(methylsulfonyl)-1-methylethylester (2S)-(9Cl), tipifarnib (Zarnestra®), and manumycin A.

Flk-1 kinase inhibitors which include without limitation 2-propenamide, 2-cyano-3-[4-hydroxy-3,5-bis(1-methylethyl)phenyl]-N-(3-phenylpropyl)-(2E-)-(9Cl).

glycogen synthase kinase-3 (GSK3) inhibitors which include without limitation indirubin-3'-monooxime.

histone deacetylase (HDAC) inhibitors which include without limitation suberoylanilide hydroxamic acid (SAHA), [4-(2-amino-phenylcarbamoyl)-benzyl]-carbamic acid pyridine-3-ylmethylester and its derivatives, butyric acid, pyroxamide, trichostatin A, oxamflatin, apicidin, depsipeptide, depudecin, trapoxin, vorinostat (Zolinza®), and compounds disclosed in WO 02/22577.

I-kappa B-alpha kinase inhibitors (IKK) which include without limitation 2-propenenitrile, 3-[(4-methylphenyl) sulfonyl]-(2E)-(9Cl).

imidazotetrazinones which include without limitation temozolomide (Methazolastone®, Temodar® and its derivatives (e.g., as disclosed generically and specifically in U.S. Pat. No. 5,260,291) and Mitozolomide.

insulin tyrosine kinase inhibitors which include without limitation hydroxyl-2-naphthalenylmethylphosphonic acid.

c-Jun-N-terminal kinase (JNK) inhibitors which include without limitation pyrazoleanthrone and epigallocatechin gallate.

mitogen-activated protein kinase (MAP) inhibitors which include without limitation benzenesulfonamide, N-[2-[[[3-(4-chlorophenyl)-2-propenyl]methyl]amino]methyl]phenyl]-N-(2-hy-droxyethyl)-4-methoxy-(9Cl).

MDM2 inhibitors which include without limitation trans-4-iodo, 4'-boranyl-chalcone.

MEK inhibitors which include without limitation butanedinitrile, bis[amino[2-aminophenyl)thio]methylene]-(9Cl).

MMP inhibitors which include without limitation Actinonin, epigallocatechin gallate, collagen peptidomimetic and non-peptidomimetic inhibitors, tetracycline derivatives marimastat (Marimastat®), prinomastat, incyclinide (Metastat®), shark cartilage extract AE-941 (Neovastat®), Tanomastat, TAA211, MMI270B or AAJ996.

mTor inhibitors which include without limitation rapamycin (Rapamune®), and analogs and derivatives thereof, AP23573 (also known as ridaforolimus, deforolimus, or MK-8669), CCI-779 (also known as temsirolimus) (Torisel®) and SDZ-RAD.

NGFR tyrosine kinase inhibitors which include without limitation tyrphostin AG 879.

p38 MAP kinase inhibitors which include without limitation Phenol, 4-[4-(4-fluorophenyl)-5-(4-pyridinyl)-1H-imidazol-2-yl]-(9Cl), and benzamide, 3-(dimethylamino)-N-[3-[(4-hydroxylbenzoyl)amino]-4-methylphenyl]-(9Cl).

p56 tyrosine kinase inhibitors which include without limitation damnacanthal and tyrphostin 46.

PDGF pathway inhibitors which include without limitation tyrphostin AG 1296, tyrphostin 9, 1,3-butadiene-1,1,3-tricarbonitrile, 2-amino-4-(1H-indol-5-yl)-(9Cl), imatinib (Gleevec®) and gefitinib (Iressa®) and those compounds generically and specifically disclosed in European Patent No.: 0 564 409 and PCT Publication No.: WO 99/03854.

phosphatidylinositol 3-kinase inhibitors which include without limitation wortmannin, and quercetin dihydrate.

phosphatase inhibitors which include without limitation cantharidic acid, cantharidin, and L-leucinamide.

protein phosphatase inhibitors which include without limitation cantharidic acid, cantharidin, L-P-bromotetramisole oxalate, 2(5H)-furanone, 4-hydroxy-5-(hydroxymethyl)-3-(1-oxohexadecyl)-(5R)-(9Cl) and benzylphosphonic acid.

PKC inhibitors which include without limitation 1-H-pyrollo-2,5-dione, 3-[1-3-(dimethylamino)propyl]-1H-indol-3-yl]-4-(1H-indol-3-yl)-(9Cl), Bisindolylmaleimide IX, Sphinogosine, staurosporine, and Hypericin.

PKC delta kinase inhibitors which include without limitation rottlerin.

polyamine synthesis inhibitors which include without limitation DMFO.

PTP1B inhibitors which include without limitation L-leucinamide.

protein tyrosine kinase inhibitors which include, without limitation tyrphostin Ag 216, tyrphostin Ag 1288, tyrphostin Ag 1295, geldanamycin, genistein and 7H-pyrrolo[2,3-d] pyrimidine derivatives as generically and specifically described in PCT Publication No.: WO 03/013541 and U.S. Publication No.: 2008/0139587.

SRC family tyrosine kinase inhibitors which include without limitation PP1 and PP2.

Syk tyrosine kinase inhibitors which include without limitation piceatannol.

Janus (JAK-2 and/or JAK-3) tyrosine kinase inhibitors which include without limitation tyrphostin AG 490 and 2-naphthyl vinyl ketone.

retinoids which include without limitation isotretinoin (Accutane®, Amnesteem®, Cistane®, Claravis®, Sotret®) and tretinoin (Aberel®, Aknoten®, Avita®, Renova®, Retin-A®, Retin-A MICRO®, Vesanoid®).

RNA polymerase II elongation inhibitors which include without limitation 5,6-dichloro-1-beta-D-ribofuranosylbenzimidazole.

serine/Threonine kinase inhibitors which include without limitation 2-aminopurine.

sterol biosynthesis inhibitors which include without limitation squalene epoxidase and CYP2D6.

VEGF pathway inhibitors, which include without limitation anti-VEGF antibodies, e.g., bevacizumab, and small molecules, e.g., sunitinib (Sutent®), sorafinib (Nexavar®), ZD6474 (also known as vandetanib) (Zactima™), SU6668, CP-547632 and AZD2171 (also known as cediranib) (Recentin™).

Examples of chemotherapeutic agents are also described in the scientific and patent literature, see, e.g., Bulinski (1997) J. Cell Sci. 110:3055-3064; Panda (1997) Proc. Natl. Acad. Sci. USA 94:10560-10564; Muhlradt (1997) Cancer Res. 57:3344-3346; Nicolaou (1997) Nature 387:268-272; Vasquez (1997) Mol. Biol. Cell. 8:973-985; Panda (1996) J. Biol. Chem. 271:29807-29812.

Other exemplary anti-cancer agents include alitretinon, altretamine, aminopterin, aminolevulinic acid, amsacrine (Amsidine®), asparaginase (crisantaspase, Erwinase®), atrasentan, bexarotene (Targretin®), carboquone, demecolcine, efaproxiral, elsamitrucin, etoglucid, hydroxycarbamide, leucovorin, lonidamine, lucanthone, masoprocol, methyl aminolevulinate, mitoguazone, mitotane (Lysodren®), oblimersen, omacetaxine (Genasense®), pegaspargase (Oncaspar®), porfimer sodium (Photofrin®), prednimustine, sitimagene ceradenovec (Cerepro®), talaporfin, temoporfin, trabectedin (Yondelis®), and verteporfin.

EXAMPLES

The following examples illustrate specific embodiments of the present invention and methods of preparation thereof. The inositol compounds described are illustrated in FIG. 1 and incorporate several design features. Compounds of group 1 include compounds A-C and comprise a deoxy inositol theme. Compounds of group 2 include compounds E and F and comprise a tethered phophoinositol-inositol theme. Compounds of group 3 include compound D and comprise a full inositol theme.

Compound A (Group 1) is a 3-deoxy phosphatidyl D-chiroinositol with one of the lipid group (—OC(O)C$_{18}$H$_{37}$) replaced with a methoxy group. This is compared to the parent deoxy phosphatidyl D-chiroinositol B (Group 1).

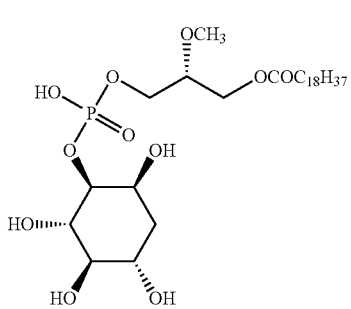

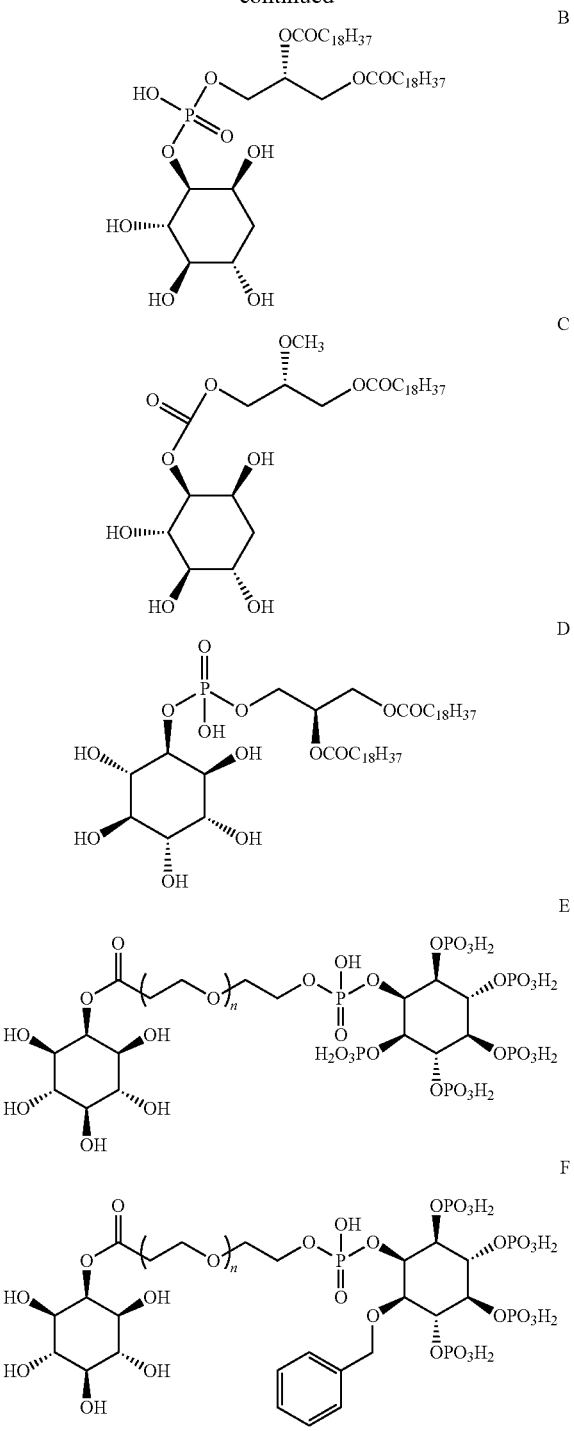

Compound C (Group 1) represents another variant of the D-chiroinositol lipid system where the phosphate group at position 1 is replaced with a carbonate.

Compound D (Group 3) represents phosphatidyl D-chiroinositol with its full complement of hydroxyl groups.

Compounds E and F (Group 2) are structures presenting both myoinositol and myoinositol phosphates that are linked together. In the case of compound F, one of the phosphate groups is replaced with a benzyl ether. The linkage in the Group 2 compounds E and F is an ethylene glycol or polyethylene glycol, one end of which has been etherified to a beta- (or more distantly removed) carbon of a propionic (or larger aliphatic) acid. The derivatized glycol linker's free OH is esterified with the phosphate of the phosphorylated inositol and the free acid function is esterified with a free OH of the unphosphorylated inositol.

In order that the invention described herein may be fully understood, the following examples are set forth. It is understood that these examples are for illustrative purposes and are not to be construed as limiting this invention in any manner. The syntheses of other compounds of the present invention are conducted in an analogous manner to ones of Examples 1-7 described below, as will be appreciated by those of ordinary skill in the art.

Example 1—Synthesis of Compound E (Group 2)

Myo-inositol and its phosphate isomers are known compounds as are the corresponding deoxy analogs thereof. Described herein is the synthesis of compound E above (a Group 2 compound). The remaining Group 2 compounds are prepared analogously to the synthesis for Compound E using the appropriate inositol isomers or deoxy inositol isomers as needed.

Figure 2:
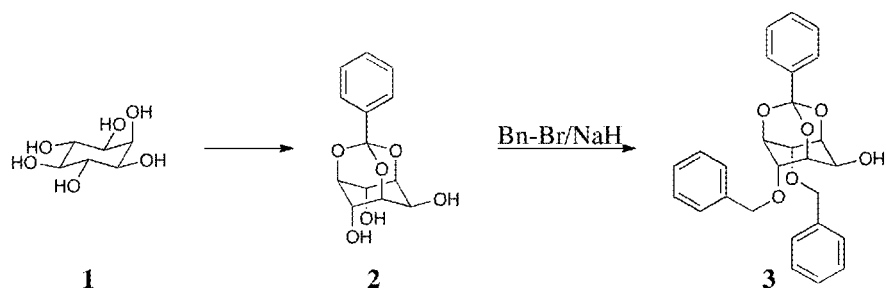
FIG. 2—Preparation of a protected inositol intermediate used in the preparation of inositol target structures is provided, in accordance with an embodiment of the present invention.

As illustrated in FIG. 2, preparation of compound E begins with commercially available myoinositol. Specifically, compound 1 is reacted with an orthoester providing compound 2 [Billington, 1989; Praveen 2001]. Conversion of compound 2 to compound 3 proceeds via reaction with sodium hydride and benzyl bromide [Billington, 1989].

Figure 3:
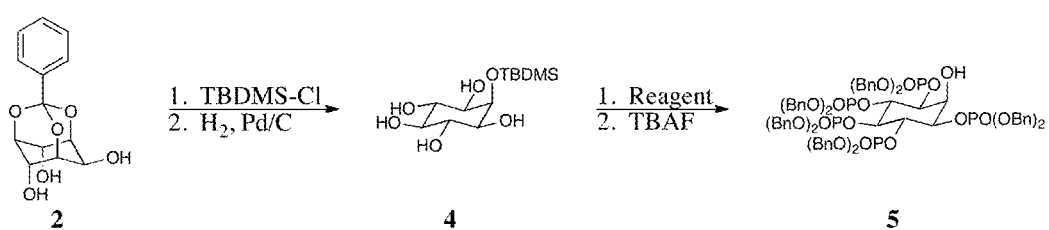
FIG. 3—Preparation of a pentaphosphate precursor to inositol target structures is provided, in accordance with an embodiment of the present invention.

As illustrated in FIG. 3, compound 2 (FIG. 1) reacts with tert-butyl dimethylsilyl chloride (TBDMS-Cl) [Lee, 2006] selectively protecting the single equatorial hydroxyl group. Subsequent cleavage of the orthobenzoate proceeds via catalytic hydrogenation yielding compound 4. Reaction of compound 4 with dibenzyl N,N-diisopropylphosphoramidite (NN-DIPA) installs five phosphate precursors [Anderson, 2010]. Subsequent treatment with tetrabutylammonium fluoride cleaves the silyl ether liberating compound 5.

Figure 4:
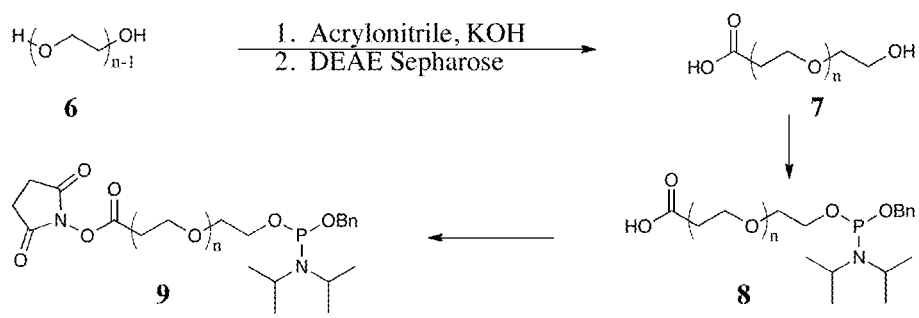
FIG. 4—Preparation of a heterobifunctional poly(ethylene)glycol reagent used in the preparation of Group 2 compounds is provided, in accordance with an embodiment of the present invention.

As illustrated in FIG. 4, polyethylene glycol, compound 6, is converted to the mono-carboxylic acid, compound 7, on treatment with acrylonitrile followed by ion exchange separation of the reaction product mixture [Harris, 1997]. Reaction of compound 7 with phosphorodiamidous acid N,N,N', N'-tetrakis(1-methylethyl)-, phenylmethyl ester yields the phosphate precursor compound 8 [Anderson, 2010]. Conversion of compound 8 to the final N-hydroxysuccinimide (NHS) ester, compound 9 proceeds on treatment of compound 8 with dicyclohexyl carbodiimide and N-hydroxysuccinimide [Harris, 1997].

Figure 5:
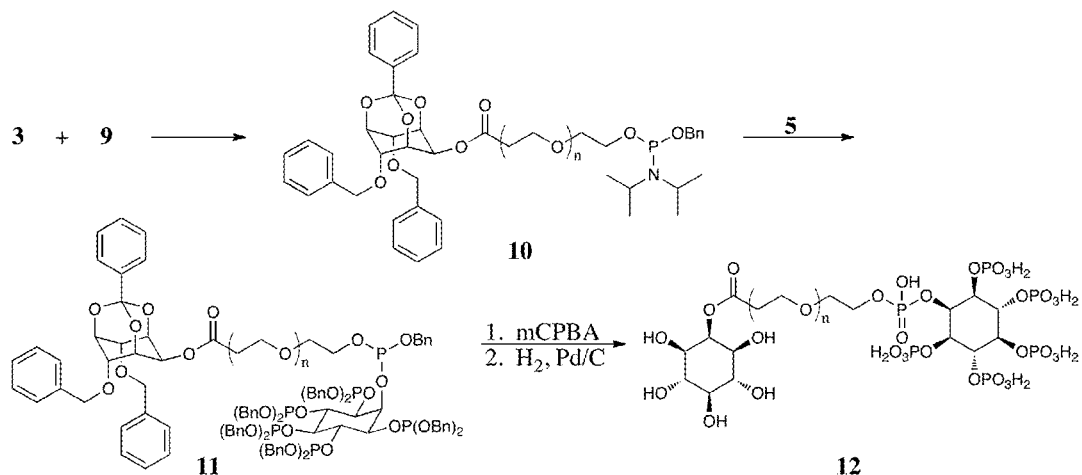
FIG. 5—Assembly and completion of Compound E is provided, in accordance with an embodiment of the present invention.

As illustrated in FIG. 5, compound 3 reacts with the NHS ester end of compound 9 yielding compound 10. Compound 10 then couples with compound 5 [Anderson, 2010] yielding compound 11. At this stage, all phosphites are oxidized to phosphates on treatment with mCPBA. Final cleavage of all benzyl groups and the orthobenzoate is proceeds via catalytic hydrogenation yielding the desired compound 12 (Compound E).

As alternatives to the chemistry presented in FIGS. 2-5, the alcohol of compound 7 (FIG. 4) is protected as a TBDMS ether and the NHS ester is formed as illustrated. The silyl alternative to compound 9 is coupled with compound 3, the TBDMS ether is cleaved and the resulting alcohol is reacted with phosphorodiamidous acid N,N,N', N'-tetrakis(1-methylethyl)-, phenylmethyl ester generating the planned compound 10 (FIG. 5).

Example 2—Synthesis of the 3-Deoxy Inositol Precursor to Compounds A, B and C (Group 1)

Compounds A, B and C are synthesized via FIGS. 6-9. All three proceed through a common intermediated (compound 23) described in FIG. 6.

Figure 6:
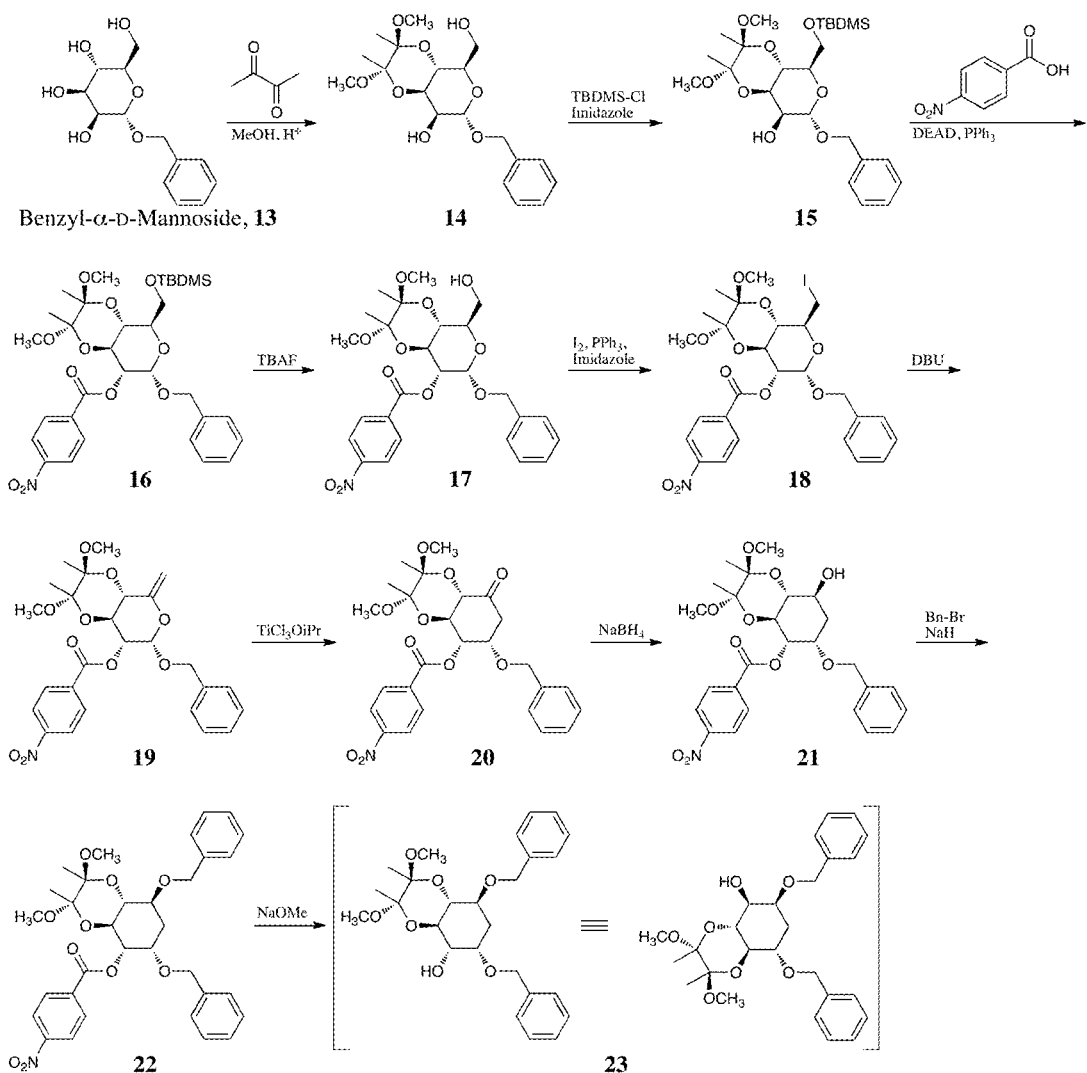
FIG. 6—Preparation of a protected deoxyinositol precursor used in the preparation of inositol target structures is provided, in accordance with an embodiment of the present invention.

As illustrated in FIG. 6, commercially available benzyl-α-D-mannoside, compound 13, reacts with 2,3-butanedione to simultaneously protect the 3- and 4-hydroxyl groups [Ley 2001]. The 6-hydroxyl group is then protected as a silyl ether leaving the 2-hydroxyl group free for subsequent Mitsunobu inversion with 4-nitrobenzoic acid. Cleavage of the silyl group from the 6-hydroxyl group yields compound 17.

Conversion of the sugar structure to the required 3-deoxyinositol continues by conversion of the 6-hydroxyl group of compound 17 to an iodide (compound 18). Elimination on treatment with DBU yield the enol ether compound 19. Finally, treatment with a Lewis acid generates the inositol compound 20 [Das 1997; Sollogoub 1998]. Reduction of the carbonyl generating compound 21 is accomplished on treatment with sodium borohydride or L-selectride [Novak 2009].

Completion of the protected 3-deoxyinositol proceeds through conversion of the free hydroxyl group to a benzyl ether (compound 22) on treatment with benzyl bromide and sodium hydride. Hydrolysis of the 4-nitrobenzoate with sodium methoxide yielding the desired compound 23.

Example 3—Synthesis of the Lipid Components of Compounds A and B (Group 1)

Figure 7:
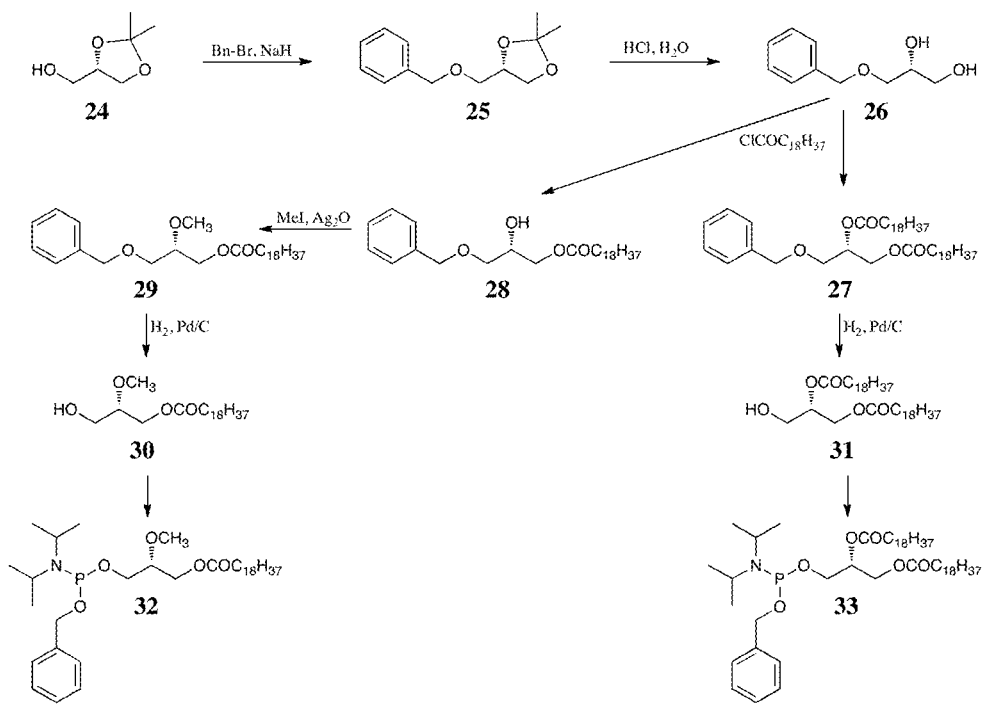
FIG. 7—Preparation of diacylglycerophosphate and monoacylmonoether glycerophosphate portions of Compounds A, B and D is provided, in accordance with an embodiment of the present invention.

As illustrated in FIG. 7, commercially available compound 24 is protected as its corresponding benzyl ether on treatment with benzyl bromide and sodium hydride. The acetonide of compound 25 is cleaved under acidic conditions yielding the desired compound 26. Depending upon the number of equivalents of nonadecanoyl chloride used, selective acylation of compound 26 is achieved at either the primary hydroxyl group (compound 28) or at both hydroxyl groups (compound 27). In the case of compound 28, reaction with methyl iodide and silver oxide yields the methyl ether, compound 29. From this point, the benzyl ether of compound 27 or compound 29 is cleaved by catalytic hydrogenation yielding compound 30 or compound 31. Finally, reaction of compound 30 or compound 31 with phosphorodiamidous acid N,N,N',N'-tetrakis(1-methylethyl)-, phenylmethyl ester [Anderson 2010] generates the required phosphate precursor compound 32 or compound 33. These compounds are used in the preparation of compounds A and B.

Example 4—Synthesis of Compound A (Group 1)

Figure 8:
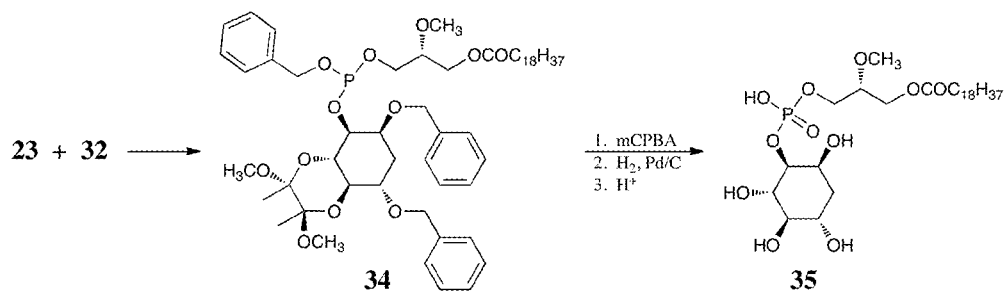
FIG. 8—Completion of Compound A is provided, in accordance with an embodiment of the present invention.

As illustrated in FIG. 8, compound 23 (FIG. 6) is coupled with compound 32 (FIG. 7) yielding the phosphite compound 34. The phosphite of compound 34 is then oxidized to a phosphate using mCPBA [Anderson 2010], the benzyl group is cleaved via catalytic hydrogenation and the diacetal is cleaved via acid hydrolysis producing the desired compound 35 (Compound A).

Example 5—Synthesis of Compound B (Group 1)

Figure 9:
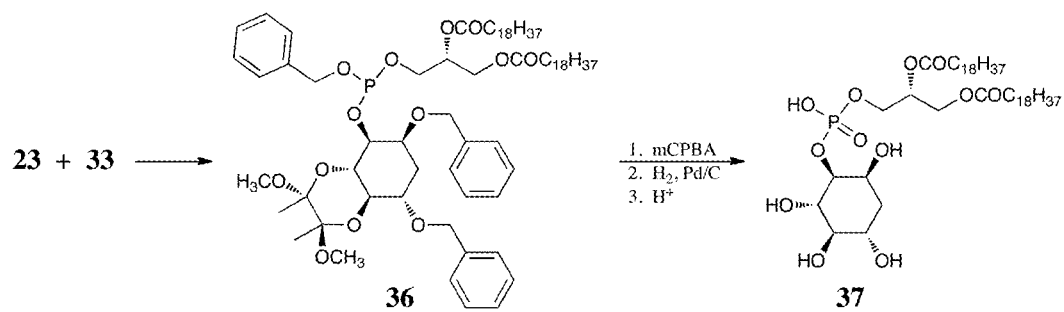
FIG. 9—Completion of Compound B is provided, in accordance with an embodiment of the present invention.

As illustrated in FIG. 9, compound 23 (FIG. 6) is coupled with compound 33 (FIG. 7) yielding the phosphite compound 36. The phosphite of compound 36 is then oxidized to a phosphate using mCPBA [Anderson 2010], the benzyl group is cleaved via catalytic hydrogenation and the diacetal is cleaved via acid hydrolysis producing the desired compound 37 (Compound B).

Example 6—Synthesis of Compound C (Group 1)

Figure 10:
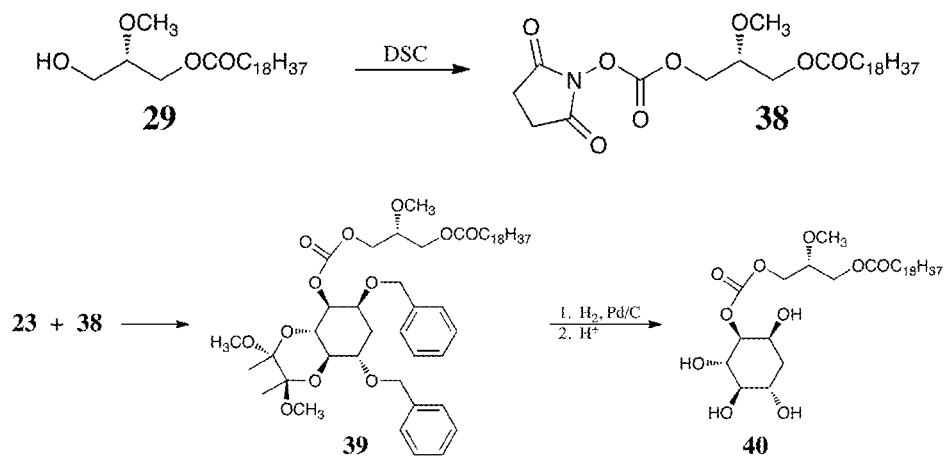
FIG. 10—Preparation of the monoacyl monoether glycerocarbonate portion of and completion of Compound C is provided, in accordance with an embodiment of the present invention.

As illustrated in FIG. 10, compound 29 (FIG. 7) is reacted disuccinimidyl carbonate to generate the succinimidyl carbonate compound 38. Compound 38 is then reacted with compound 23 (FIG. 6) to yield the desired carbonate compound 39. The benzyl groups are removed via catalytic hydrogenation and cleavage of the diacetal is achieved on acidic hydrolysis giving the final compound 40 (Compound C).

Example 7—Synthesis of Compound D (Group 3)

The present invention includes certain analogs of the Group 1 compounds. These Group 3 analogs differ from the Group 1 compounds only in that while Group 1 compounds have a "deoxy" position, Group 3 analogs have a full complement of hydroxy groups. One such compound is compound D (FIG. 1).

Figure 11:
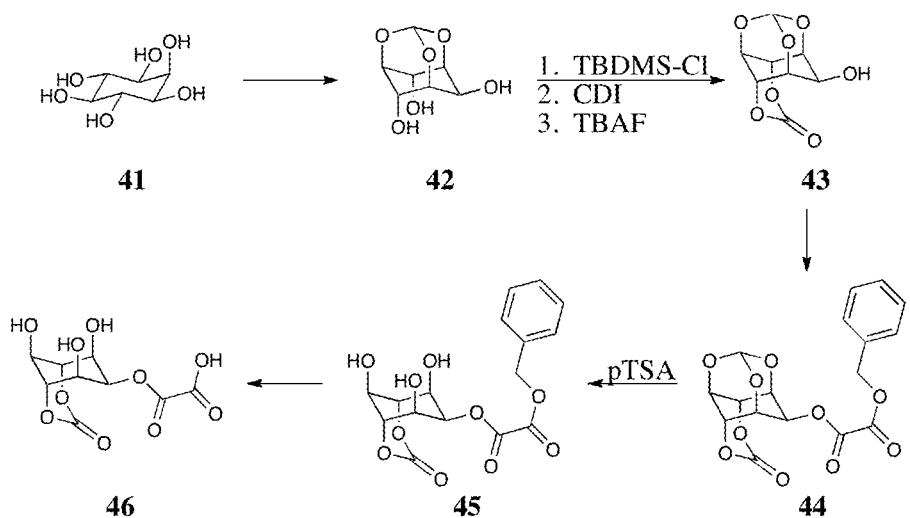
FIG. 11—Preparation of a protected inositol intermediate used in the preparation of inositol target structures is provided, in accordance with an embodiment of the present invention.

As illustrated in FIG. 11, commercially available myo-inositol, compound 41 reacts with trimethyl orthoformate providing compound 42 [Billington 1989; Praveen [2001]. Conversion of compound 42 to cyclic carbonate compound 43 proceeds via initial protection of the equatorial hydroxyl group with a tert-butyl dimethylsilyl ether followed by carbonate formation with carbonyl diimidazole [Lee 2006] and silyl ether cleavage with tetrabutylammonium fluoride. Coupling of compound 43 with oxalic acid monobenzyl ester yields compound 44. Removal of the orthoformate using para-toluenesulfonic acid [Lee 2006] yields compound 45. Cleavage of the benzyl ester proceeds via catalytic hydrogenation yielding compound 46.

Figure 12:
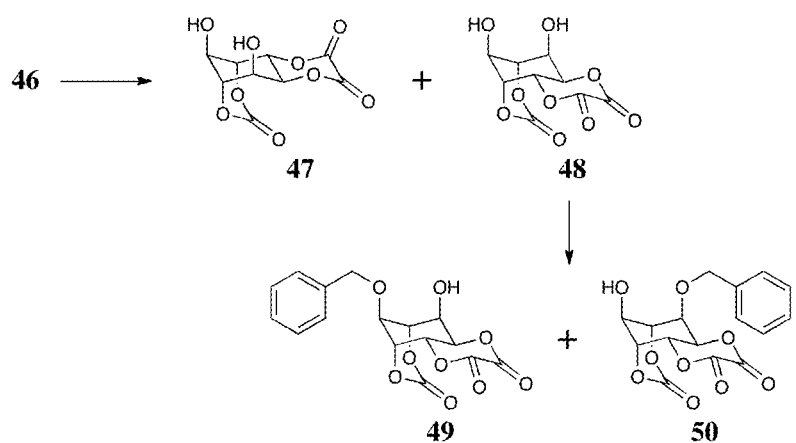
FIG. 12—Preparation of a protected inositol intermediate used in the preparation of inositol target structures is provided, in accordance with an embodiment of the present invention.

As illustrated in FIG. 12, compound 46 yields a mixture of compound 47 and compound 48 when subjected to Mitsunobu conditions. These compounds are expected separated by chromatographic means. Isolated compound 47 and isolated compound 48 are separately treated with lithium hydroxide to remove both the oxalate diester and the carbonate. The NMR and optical rotation of deprotected compound 48 matches the NMR and optical rotation of authentic and commercially available chiroinositol. Isolated compound 48 is then treated with sodium hydride and benzyl bromide is yielding a mixture of compound 49 and compound 50 [Billington 1989]. These compounds are separated by chromatographic means. Isolated compound 49 is advanced according to FIG. 13 and isolated compound 50 is advanced according to FIG. 14.

Figure 13:
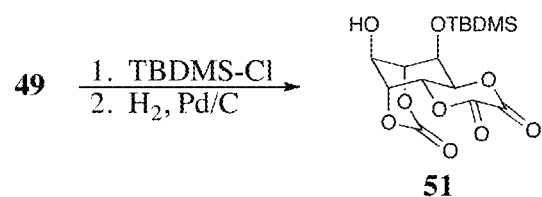
FIG. 13—Preparation of a protected inositol intermediate used in the preparation of inositol target structures is provided, in accordance with an embodiment of the present invention.

As illustrated in FIG. 13, compound 49 is converted to a silyl ether utilizing tert-butyl dimethylsilylchloride. Subsequent catalytic hydrogenation cleaves the benzyl ether liberating compound 51.

Figure 14:
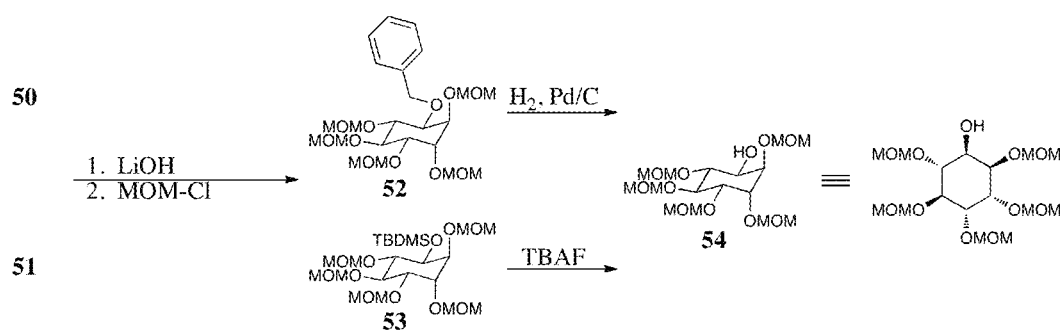
FIG. 14—Preparation of a protected inositol intermediate used in the preparation of inositol target structures is provided, in accordance with an embodiment of the present invention.

As illustrated in FIG. 14, compound 50 (FIG. 12) and compound 51 (FIG. 13) are separately advanced by initial hydrolysis of the oxalyl diester and cyclic carbonate with lithium hydroxide followed by conversion to the penta-MOM-protected compounds 52 and 53, respectively. The benzyl group of compound 52 is cleaved via catalytic hydrogenation and the silyl ether of compound 53 is cleaved on treatment with tetrabutylammonium fluoride. Utilizing these reactions, compound 54 is produced from both compound 52 and compound 53.

Figure 15:
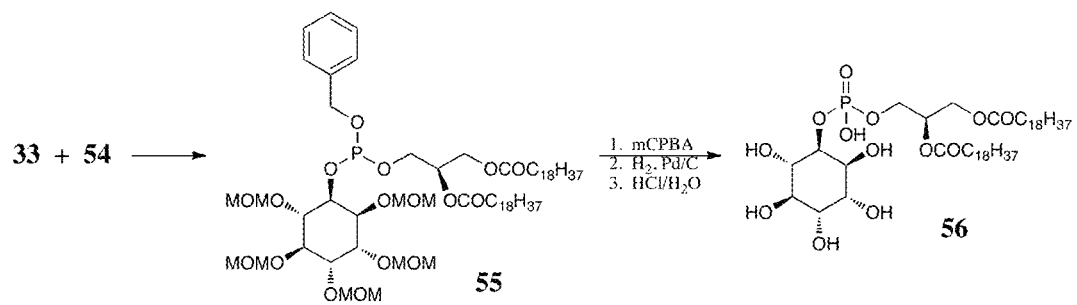
FIG. 15—Completion of Compound D is provided, in accordance with an embodiment of the present invention.

As illustrated in FIG. 15, Compound D is completed by coupling compound 33 (FIG. 7) with compound 54 (FIG.

14) yielding compound 55 [Anderson 2010]. Oxidation of the phosphite to a phosphate is proceeds using mCPBA [Anderson 2010]. Cleavage of the benzyl ester proceeds via catalytic hydrogenation. Final removal of the methoxymethyl ethers is expected on treatment with acid yielding the target compound 56 (Compound D).

Example 8—General Evaluation of Compounds

Compounds of the present invention are evaluated using standard methods such as NMR spectroscopy UV/VIS spectroscopy, IR spectroscopy and mass spectrometry. Purity of compounds of the present invention is established using standard column chromatography, reverse phase column chromatography and HPLC methods. Compounds of the present invention are evaluated for their activities in cancer cell line assays including a panel of 60 cell lines offered by the Developmental Therapeutics Program of the National Cancer Institute. Compounds are also evaluated in animal models such as mouse xenograft models as generally described in Cheng et al. Cancer Research 2012, 72(10): 2634-44. To test the activities of compounds, standard assays and custom developed assays are used.

Example 9—Evaluation of PEG-Linked Compounds in a Cell-Based Assay

The activities of compounds XI and XII are evaluated using one or more of the various assays described in Example 8 including, but not limited to these assays. For example, cell culture and reagents MCF-7 cells are cultured in DMEM/Ham's F12 medium (1:1) supplement with 5% fetal calf serum (FCS), glutamine (300 mg/ml), penicillin (100 IU/ml), and streptomycin (100 mg/ml). All SCLC cell lines are grown in RPMI 1640 with 25 mM HEPES supplement with 10% heat inactivated fetal bovine serum (FBS). The human ovarian cancer cell lines SKOV-3 and OVCAR-432 and the human colocarcinoma cell line SW620 grow in RPMI 1640 supplemented with 10% FCS. COS-7 cells are maintained in DMEM supplemented with 10% CS. Incorporation of compounds with formula XI or XII in SCLC cells Ca. 1 3 107 SCLC cells, are grown, transferred, and disaggregated as described below, and pelleted by centrifugation (50 g, 5 min) and resuspend to 1 ml in medium containing 0.5% FCS. Following a 12-h incubation at 37° C., 50 mM cold (unlabeled) Ins (1,3,4,5)P4 and ca. 400,000 dpm [3H]— A compound with Formula XI or XII is added. After a 20-min incubation at 37° C., the cells are pelleted by being briefly (10 s) centrifuged in a microcentrifuge, then rapidly washed twice in phosphate buffered salt solution (PBS) containing 0.3% bovine serum albumin (BSA), and killed by the addition of 750 ml cold (220° C.) methanol/1N HCl (1:1). Following the addition of further methanol and chloroform, to form a two-phase extraction of aqueous (upper) and organic (lower) phases the aqueous phase is lyophilized and analyzed by high-performance liquid chromatography (HPLC). Parallel extraction and HPLC analysis is also carried out on the medium from the incorporation to determine the stability and purity of the added [3H]-compound with formula XI or XII through the incubation.

Example 10—MCF-7 Cell Assay

Assays are performed in 24-well plates. Serum-starved cells are pretreated with compounds with formula XI, XII, XIII, XIV, XV or XVI for 20 min and then stimulated with insulin-like growth factor-1 (IGF-1). After 20 h of incubation, [3H]-labeled thymidine (2 mCi/ml) is added. Twenty-six hours after the addition of IGF-1, cells are fixed with 10% trichloroacetic acid, washed in water, and lysed in 0.1 N NaOH. The levels of [3H]-thymidine labeling are then quantified by liquid scintillation counting.

Example 11—SCLC Cell Assay

Five days after passage, SCLC cells are transferred to SITA medium (RPMI 1640 medium with 25 mM HEPES supplemented with 30 nM selenium, 5 mg/ml insulin, 10 mg/ml 1180 Vol. transferrin) and culture for a further 2 days. The cells are washed twice and resuspended in fresh SITA medium before being gently disaggregated by two passes through a 21-gauge needle into an essentially single-cell suspension. Cells (13105) are seeded into 24-well plates in SITA medium and incubated for 4 h before the addition of a compound of formula XI, XII, XIII, XIV, XV or XVI. Cell numbers are determined on or about day 9, after disaggregation into single-cell suspensions, using a Coulter Counter ZM link to a Coulter Channelizer 256, according to the manufacturer instructions.

Example 12—Human Ovarian Cancer Cell Assay

The human ovarian cancer cell lines SKOV-3 and OVCAR-432 and the human colocarcinoma cells (SW620) are seeded into 96-well plates and kept in medium with 0.5% FCS for 12 h before treatment. The treatments with LY294002 (10 mM) and a compound of formula XI, XII, XIII, XIV, XV or XVI is carried out in medium plus 0.5% FCS. All the compounds to be tested are initially dissolved in DMSO with the incubations containing a constant 0.5% DMSO. Dimethylthiazol-2yl)-2,5-diphenyltetrazolium bromide (MTT) analysis is performed 72 h after the treatments, and the values are described as percentages of inhibition of the control, DMSO-treated cell growth.

Example 13—Clonogenic Assay

Five days after passage, SCLC cells are washed and resuspended in SITA medium. Cells are disaggregated (as above); 1 3 104 viable cells are mixed with SITA containing 0.3% (w/v) agarose and the compound of formula XI, XII, XIII, XIV, XV or XVI at the concentrations indicated, and are layered over a solid base of 0.5% (w/v) agarose in 35-mm plastic dishes. The cultures are incubated in a humidified 5% CO2 incubator at 37° C. for 21 days and then stained with the vital stain nitroblue tetrazolium. Colonies of 120 mm will be counted under a microscope.

Example 14—Immunofluorescence Assay cDNA encoding the PKB/Akt PH domain is subcloned into the green fluorescent protein (GFP) fusion protein expression vector pEGFP-C1 (CLONTECH, Palo Alto, Calif.), using a BglII and EcoRI sites for expression of an EGFP-PH domain fusion protein in mammalian cells. COS-7 cells are seeded onto 12-mm circular glass coverslips in wells of 6-well plates and transfected with 1 mg of the EGFP fusion protein. LipofectAMINE (Life Technologies, Grand Island, N.Y.) is used for the transfections, according to the manufacturer suggestions. After preincubations without or with a compound of formula XI, XII, XIII, XIV, XV or XVI about s (50 mM), the cells are stimulated with growth factors, washed in PBS, fixed in 4% paraformaldehyde/PBS, and mounted for fluorescence microscopy. Razzini, et al 2000.

Example 15—Pancreatic Tumor Cell Assay

Pancreatic tumor lines PANC1 and MIAPACA are studied according to Somasundar et al. 2005.

Example 16—Dosages and Administration

The compound of Formula XI is administered orally to a patients A-D in an amount as set forth in the following table 1 in two divided doses daily, Patients A and B are children, while patients C and D are adults.

TABLE 1

| Patient A | Patient B | Patient C | Patient D |
|---|---|---|---|
| 1.5 grams | 3.0 grams | 6.0 grams | 9.0 grams |
| 3.0 grams | 6.0 grams | 9.0 grams | 1.5 grams |

The compound of Formula XI is administered to a patient at a dose of 40 mg/m2 every 4 weeks (for an overall dose intensity of 10 mg/m2 per week)

The compound of Formula XI is administered to a patient biweekly at the dose of 15 mg/m2 for four administrations Compounds A-D Compounds A-D are administered to patients as in the following table 2. The amount given to patients E-K and AA is administered intravenously in divided doses over 2-5 days. Patients L-S receive intravenous administration every 7-10 days, while Patients, while patients T-Z and AB are treated twice weekly

TABLE 2

| | Regimen |
|---|---|
| Patient E | 40 mg/kg Compound A |
| Patient F | 50 mg/kg Compound A |
| Patient G | 40 mg/kg compound B |
| Pateient H | 40 mg/kg compound B |
| Patient I | 40 mg/kg compound C |
| Patient J | 50 mg/kg compound C |
| Patient K | 40 mg/kg compound D |
| Patient AA | 50 mg/kg compound D |
| Patient L | 10/kg compound A |
| Patient M | 15 mg/kg compound A |
| Patient N | 10 mg/kg compound B |
| Patient O | 15 mg/kg compound B |
| Patient P | 10 mg/kg Compound C |
| Patient Q | 15 mg/kg compound C |
| Patient R | 10 mg/kg compound D |
| Patient S | 15 mg/kg compound D |
| Patient T | 3 mg compound A |

TABLE 2-continued

| | Regimen |
|---|---|
| Patient U | 5 mg compopund A |
| Patient V | 3 mg compound B |
| Patient W | 5 mg compound B |
| Patient X | 3 mg compound C |
| Patient Y | 5 mg compound C |
| Patient Z | 3 mg compound D |
| Patient AB | 5 mg compound D |

Oral Administration dosing is in the range of 1 to 5 mg/kg/day for both initial and maintenance dosing of compounds A-D For Direct Injection: Compounds A-D are prepared for parenteral use by adding 0.9% sterile sodium chloride solution. Solutions of drugs are injected intravenously, intramuscularly, intraperitoneally, or intrapleurally if constituted by adding 0.9% sterile sodium chloride solution.

For Infusion: Compounds A, B, C, D are prepared for parenteral use by infusion using any of the following methods:

A. 0.9% sterile sodium chloride may be infused without further dilution. Compounds constituted with 0.9% sterile sodium chloride are infused following further dilution in the following: Dextrose Injection, USP (5% dextrose) Dextrose and Sodium Chloride Injection, USP (5% dextrose and 0.9% sterile sodium chloride)

B. 5% Dextrose and Ringer's Injection Lactated Ringer's Injection, USP Sodium Chloride Injection, USP (0.45% sterile sodium chloride) Sodium Lactate Injection, USP (1/6 molar sodium lactate)

C. Compounds A, B, C D sterile powder form are prepared for parenteral use by infusion by adding Sterile Water Compounds in sterile powder constituted in Sterile Water for Injection is further diluted in one of the following: Dextrose Injection, USP (5% dextrose) Dextrose and Sodium Chloride Injection, USP (5% dextrose and 0.9% sterile sodium chloride) 5% Dextrose and Ringer's Injection Lactated Ringer's Injection, USP D. Sodium Chloride Injection, USP (0.45% sterile sodium chloride) Sodium Lactate Injection, USP (1/6 molar sodium lactate)

All patents and publications mentioned in this specification are herein expressly incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

The invention claimed is:

1. A compound represented by the structure of formula XI,

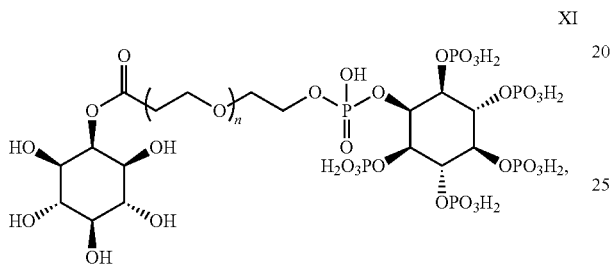

XI or formula XII,

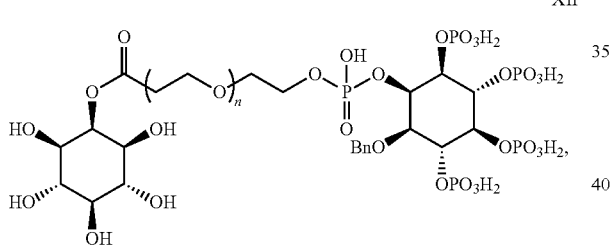

XII wherein n is an integer from 1-6.

2. A pharmaceutical composition comprising at least one compound of claim 1 and at least one pharmaceutically acceptable excipient and/or carrier.

3. The pharmaceutical composition of claim 2, further comprising at least one additional anticancer therapeutic agent other than the compound of formula XI or XII.

4. A method of preparing a compound of formula I,

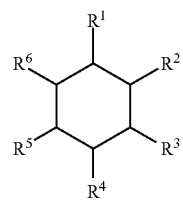

I comprising:
reacting a compound of formula III with a compound of formula IV producing a compound of formula V;

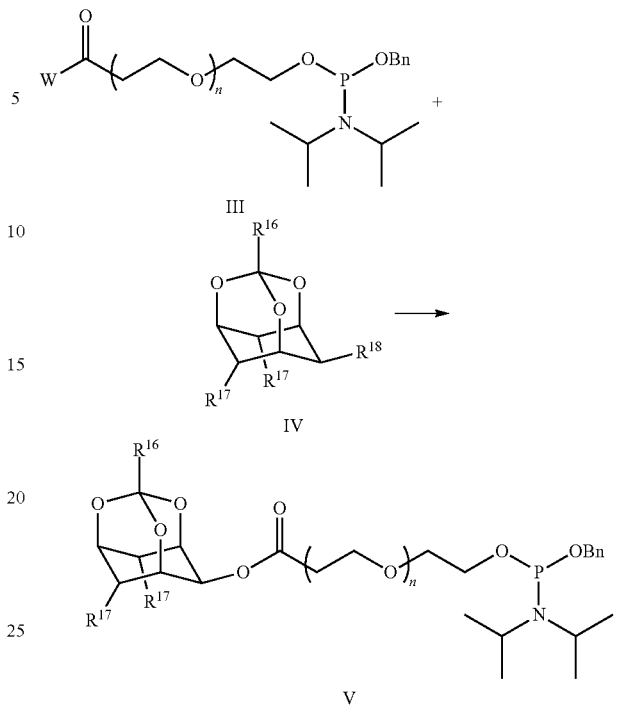

reacting a compound of formula V with a compound of formula VI producing a compound of formula VII;

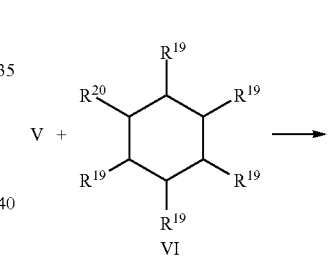

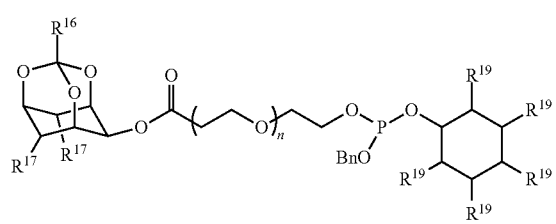

VII oxidizing a phosphite to a phosphate; and
cleaving all protecting groups,
wherein:
one of $R^1$-$R^6$ is —O-Y and five of $R^1$-$R^6$ are OH;
each of $R^1$-$R^6$ may be independently in an axial or an equatorial orientation;
Y is —C(=O)—$R^8$;
$R^8$ is —(CH$_2$CH$_2$O—)$_x$—CH$_2$CH$_2$—Z;
x is an integer from 1-6;

Z is a structure of formula II:

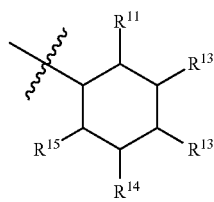

wherein:

each of four of $R^{11}$ through $R^{15}$ is —O—P(=O)(OH)$_2$;

one of $R^{11}$ through $R^{15}$ is selected from benzyloxy and —O-P(=O)(OH)$_2$;

each of substituent on the ring of formula II may be independently in either an axial or an equatorial orientation, W is a leaving group selected from NHS, 4-nitrophenol, imidazole, HOBT and halide;

$R^{16}$ is H, $C_1$-$C_6$ alkyl or phenyl;

each $R^{17}$ is —O-benzyl, —O-TMS, —O-TBDMS, —O-TBDPS, —O-(4-methoxybenzyl), acetoxy or —O-MOM;

$R^{18}$ is OH;

each $R^{19}$ is —OP(O)(OBn)$_2$;

$R^{20}$ is OH;

each of $R^{17}$, $R^{18}$, $R^{19}$ and $R^{20}$ may be independently in an axial or an equatorial orientation; protecting groups are independently selected from benzyl ether, benzyl ester, benzyl phosphate, orthobenzoate, orthoformate, TBDMS, and MOM; and n is an integer from 1-6.

5. The method according to claim 4 for the preparation of a compound of formula XI

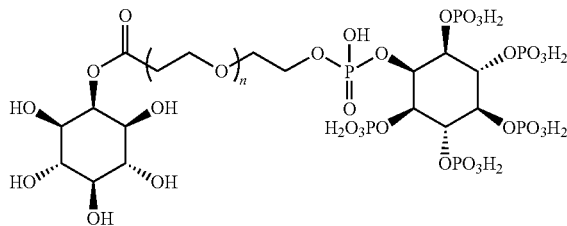

wherein n is an integer from 1-6.

6. The method according to claim 4 for the preparation of a compound of formula XI

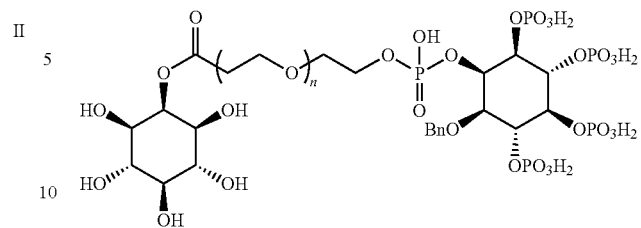

wherein n is an integer from 1-6.

7. A method of treating cancer comprising administering a compound of formula XI

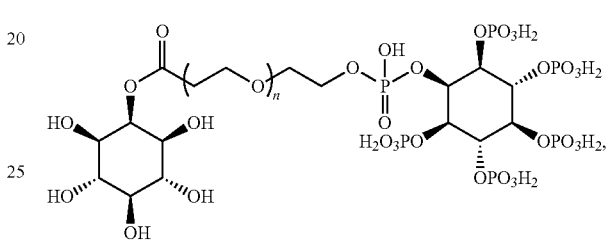

or formula XII,

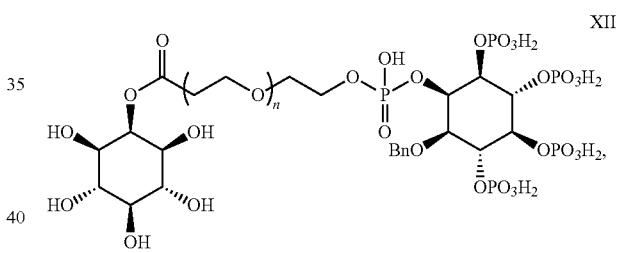

to a patient in need thereof.

8. The method of claim 7, wherein the compound of formula XI or XII is administered alone.

9. The method of claim 7, wherein the compound of formula XI or XII is administered in a formulation.

10. The method of claim 7, wherein the compound of formula XI or XII is administered topically.

11. The method of claim 7, wherein the compound of formula XI or XII is administered orally.

12. The method of claim 7, wherein the compound of formula XI or XII is administered intravenously.

13. The method of claim 7, wherein the compound of formula XI or XII is administered rectally.

* * * * *